US008435291B2

(12) United States Patent
Wiens et al.

(10) Patent No.: US 8,435,291 B2
(45) Date of Patent: May 7, 2013

(54) METHOD AND APPARATUS FOR IN-SITU ADJUSTABILITY OF A MIDDLE EAR PROSTHESIS

(75) Inventors: Gloria Jean Wiens, Gainesville, FL (US); Patrick J. Antonelli, Gainesville, FL (US); Troy Benjamin Rippere, Gainesville, FL (US); Koustubh Jayaprakash Rao, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 175 days.

(21) Appl. No.: 12/936,036

(22) PCT Filed: Jun. 22, 2009

(86) PCT No.: PCT/US2009/048177
§ 371 (c)(1),
(2), (4) Date: Nov. 10, 2010

(87) PCT Pub. No.: WO2009/155610
PCT Pub. Date: Dec. 23, 2009

(65) Prior Publication Data
US 2011/0046731 A1   Feb. 24, 2011

Related U.S. Application Data

(60) Provisional application No. 61/074,444, filed on Jun. 20, 2008.

(51) Int. Cl.
*A61F 2/18*   (2006.01)
*H04R 25/00*   (2006.01)

(52) U.S. Cl.
USPC ............................................. 623/10; 600/25

(58) Field of Classification Search ................... 623/10; 600/25
See application file for complete search history.

(56) References Cited

U.S. PATENT DOCUMENTS

| 4,601,723 A | 7/1986 | McGrew |
| 4,676,796 A | 6/1987 | Merwin et al. |

(Continued)

FOREIGN PATENT DOCUMENTS

| BG | 65712 B1 | 8/2009 |
| WO | WO-90-11737 A1 | 10/1990 |

OTHER PUBLICATIONS

Dalchow, C.V., et al., "Reconstruction of the Ossicular Chain with Titanium Implants," *Otolaryngology—Head and Neck Surgery*, Dec. 2001, pp. 628-630, vol. 125, No. 6.

(Continued)

*Primary Examiner* — David Isabella
*Assistant Examiner* — Yashita Sharma
(74) *Attorney, Agent, or Firm* — Saliwanchik, Lloyd & Eisenschenk

(57) ABSTRACT

Embodiments provide a middle ear prosthesis that can be adjusted in situ. The middle ear prosthesis can be inserted into the middle ear of a patient and then, after surgery, the length of, or distance between the end resting on the malleus and the end resting on the stapes, can be adjusted without the need to touch the prosthesis through a surgical intervention. A middle ear prosthesis can include a first element having a first interconnecting end and a malleus end, for resting on a malleus or tympanic membrane, and a second element having a second interconnecting end and a stapes end, for resting on a stapes, where the first and second interconnecting ends interconnect with each other. External forces can be applied to a clamp to actuate release of the clamp and allow for adjustment of the length of the prosthesis in situ.

71 Claims, 26 Drawing Sheets

U.S. PATENT DOCUMENTS

| | | | |
|---|---|---|---|
| 4,740,209 | A | 4/1988 | Gersdorff |
| 4,901,353 | A | 2/1990 | Widin |
| 4,957,507 | A | 9/1990 | Lenkauskas |
| 5,180,391 | A | 1/1993 | Beoni |
| 6,168,625 | B1 | 1/2001 | Prescott |
| 6,190,305 | B1 | 2/2001 | Ball et al. |
| 6,432,139 | B1 * | 8/2002 | Elies et al. ............ 623/10 |
| 6,786,860 | B2 * | 9/2004 | Maltan et al. ............ 600/25 |
| 6,942,696 | B1 | 9/2005 | White et al. |
| 7,025,785 | B1 | 4/2006 | Boyev |
| 7,190,247 | B2 | 3/2007 | Zimmerling |
| 7,238,202 | B2 | 7/2007 | Steinhardt et al. |
| 7,288,113 | B2 | 10/2007 | Reitan et al. |
| 2001/0031908 | A1 | 10/2001 | Buschek et al. |
| 2003/0097178 | A1 | 5/2003 | Roberson et al. |
| 2007/0055372 | A1 | 3/2007 | Prescott et al. |
| 2007/0150057 | A1 | 6/2007 | Kurz et al. |
| 2007/0154030 | A1 | 7/2007 | Moses |
| 2008/0188707 | A1 | 8/2008 | Bernard et al. |
| 2009/0149697 | A1 | 6/2009 | Steinhardt et al. |

OTHER PUBLICATIONS

Fisch, U., et al., "A New L-Shaped Titanium Prosthesis for Total Reconstruction of the Ossicular Chain," *Otology & Neurotology*, Nov. 2004, pp. 891-902, vol. 25, No. 6.

Lederman, L., "Tech News: Robotics," *BioTechniques*, Sep. 2007, pp. 273-277, vol. 43, No. 3.

Lord, R.M., et al., "An Anatomically Shaped Incus Prosthesis for Reconstruction of the Ossicular Chain," *Hearing Research*, Jul. 2000, pp. 141-148, vol. 145, No. 1-2.

Zenner, H.P., et al., "Acoustomechanical Properties of Open TTP® Titanium Middle Ear Prostheses," *Hearing Research*, 2004, pp. 36-46, vol. 192, No. 1-2.

Zenner, H.P., et al., "Open Tübingen Titanium Prostheses for Ossiculoplasty: A Prospective Clinical Trial," *Otology & Neurotology*, Sep. 2001, pp. 582-589, vol. 22, No. 5.

\* cited by examiner

METHOD AND APPARATUS FOR IN-SITU ADJUSTABILITY OF A MIDDLE EAR PROSTHESIS

CROSS-REFERENCE TO RELATED APPLICATIONS

The present application is the U.S. national stage application of International Patent Application No. PCT/US2009/048177 filed Jun. 22, 2009 which claims the benefit of U.S. Provisional Application Ser. No. 61/074,444, filed Jun. 20, 2008, which is are hereby incorporated by reference herein in their entireties, including any figures, tables, or drawings.

BACKGROUND OF INVENTION

The middle ear consists of the tympanic membrane (eardrum) 31 and three small bones, the malleus ("hammer"), the incus ("anvil), and the stapes ("stirrup"). When the small bones do not function properly, were damaged by a disease process, or were not formed properly during development, surgery can be performed to insert a middle ear prosthesis to replace or augment the bones.

However, when a patient undergoes middle ear surgery, a surgeon cannot generally tell how well the patient will hear after the surgery. Often, due to a variety of factors, the length of the middle ear prosthesis needs to be adjusted after the surgery. For example, each patient heals differently, and scar tissue forms differently, leading to a need for the length of the prosthesis to be adjusted.

Heinz-Kurz marketed the first titanium middle ear implant. These implants were originally produced as non-adjustable devices. This required storage and production of total ossicular repair prostheses (TORPs) and partial ossicular repair prostheses (PORPs) of a vast array of sizes to cover all possibilities for all patients. TORPs typically have a length in the range of 3 mm to 6 mm, and PORPs typically have a length in the range of 2 mm to 3 mm. The Heinz-Kurz prostheses were produced in sizes having lengths differing in increments of a quarter of a millimeter.

Spiggle & Theis introduced adjustable titanium middle ear implants in 1998. The heads of the implants were removable to allow the surgeon to manually trim the device to the desired length. Heinz-Kurz also produced adjustable implants. The TTPT™-VARIAC System of Heinz-Kurz includes a sizing disk that attaches to the prosthesis to assist in determining the fit for the patient. The sizing disk contains indentations with various depths to hold the prosthesis during the sizing procedure.

Currently, middle ear prostheses exist where the length of the prostheses can be shortened, such as those discussed above. When the length of one of these prostheses needs to be altered, the patient has another surgery and has the prosthesis removed. Once the surgeon removes the prosthesis, a shorter or longer prosthesis that is estimated to be the proper length is inserted into the patient. If the surgery is done under local anesthesia (i.e., the patient is alert), the patient then informs the doctor if he or she can hear better or not. If not, the process is repeated until the patient's hearing is satisfactory. Additionally, if during one of these iterations the patient had better hearing before the prosthesis was cut, that prosthesis is discarded and a replacement prosthesis of a longer length is inserted. If the surgery is done under general anesthesia (i.e., the patient is asleep), it is not possible to accurately predict the post-operative hearing result.

Thus, a middle ear prosthesis that is adjustable in situ and a method for adjusting a middle ear prosthesis in situ can reduce the number of surgeries patients need to have, the number of prostheses used, and/or allow accurate adjustment of the middle ear prosthesis.

BRIEF SUMMARY

Embodiments of the present invention provide a middle ear prosthesis that can be adjusted in situ. Embodiments of the invention also relate to a method for adjusting a middle ear prosthesis in situ. In specific embodiments, the middle ear prosthesis can be inserted into the middle ear of a patient during surgery and then, after the surgery, the length of, or distance between the end resting on the malleus and the end resting on the stapes, can be adjusted without the need to touch the prosthesis through a surgical intervention. A middle ear prosthesis can include a first element 1 having a first interconnecting end 3 and a malleus end 9, for resting on a malleus or tympanic membrane, and a second element 5 having a second interconnecting end 7 and a stapes end 11, for resting on a stapes (either capitulum or footplate), where the first and second interconnecting ends interconnect with each other. The first element can incorporate an outer cylinder with an approximately cylindrical head 9, at the malleus end, and the second element can include an inner cylinder with an approximately conical foot 11, acting as the stapes end. When the prosthesis is implanted in a patient, the head 9 of the outer cylinder can rest on the malleus or tympanic membrane and the foot 11 of the inner cylinder can rest on the stapes capitulum or footplate. The inner cylinder can be inserted into the outer cylinder and inhibited from sliding by a clamp 15 with a compliant portion 17. External forces can be applied to the clamp 15 to actuate release of the clamp 15 and allow for adjustment of the length of the prosthesis in situ.

For example, in one embodiment, the clamp 15 can have magnetic material on its distal ends, and an external magnetic field can be applied to move the clamp 15 and release the cylinders allowing a change in the length of the prosthesis. In a specific embodiment, actuation can also be effected via a post-auricularly positioned induction coil.

Additional embodiments and advantages of the present invention will be described below and will be apparent to a skilled artisan from the detailed description, the figures, and the claims.

DETAILED DISCLOSURE

Embodiments of the present invention provide a middle ear prosthesis that can be adjusted in situ. Embodiments of the invention also relate to a method for adjusting a middle ear prosthesis in situ. In specific embodiments, the middle ear prosthesis can be inserted into the middle ear of a patient during surgery and then, after the surgery, the length of, or distance between the ends of the prosthesis can be adjusted without the need to touch the prosthesis. In a specific embodiment the ends of the prosthesis can rest on the malleus and the staples respectively.

Figure 14A:
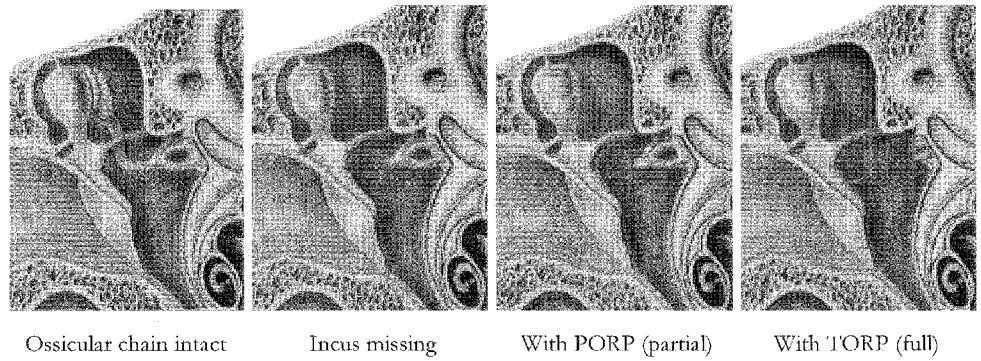
FIG. 14A shows an intact ossicular chain; an ossicular chain with the incus missing; an ossicular chain with the stapes intact and functional and the incus missing, having a partial implant (PORP); and an ossicular chain with the stapes not intact and functional, having a total implant (TORP) to replace the stapes and incus.
Figure 14B:
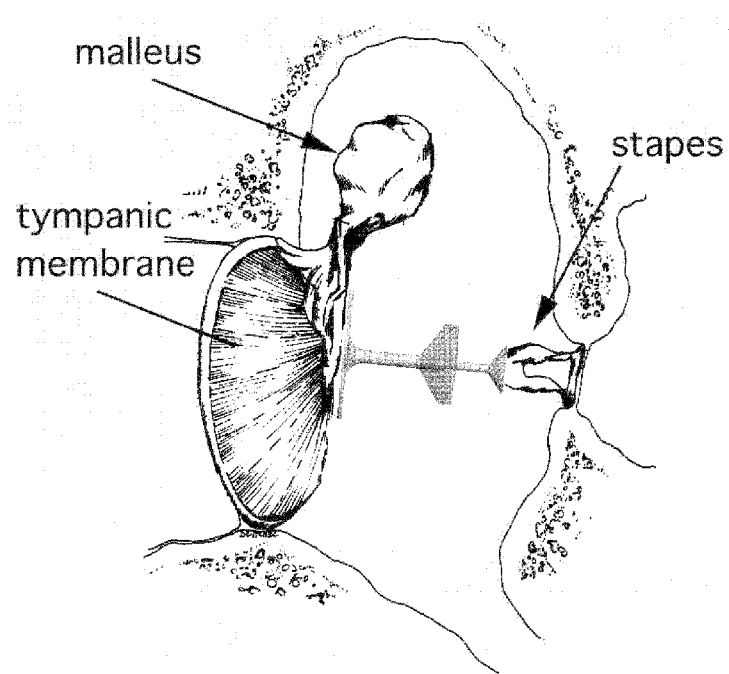
FIG. 14B shows a prosthesis on the malleus and the incus, in accordance with an embodiment.

A middle ear prosthesis can include a first element 1 having a first interconnecting end and a first distal end, and a second element 5 having a second interconnecting end and a second distal end, where the first and second interconnecting ends interconnect with each other. The first element can incorporate an outer cylinder with a broad, optionally circular or elliptical shaped head 9 at the first distal end, for contacting the malleus or tympanic membrane, and the second element can incorporate an inner cylinder with an approximately conical foot 11 at the second distal end for contacting the stapes capitulum or footplate. In a specific embodiment, head 9 can be approximately cylindrical. When the prosthesis is implanted in a patient, the head 9 of the outer cylinder can rest on the malleus, other bone of the middle ear, or eardrum, and the foot 11 of the inner cylinder can rest on the stapes (as shown in FIG. 14B) or other bone of the middle ear. The inner cylinder can be inserted into the outer cylinder and inhibited from sliding by a clamp 15 with a compliant portion 17. External forces can be applied to the clamp 15 to actuate movement of the clamp 15 and allow for adjustment of the length of the prosthesis in situ.

Figure 1:
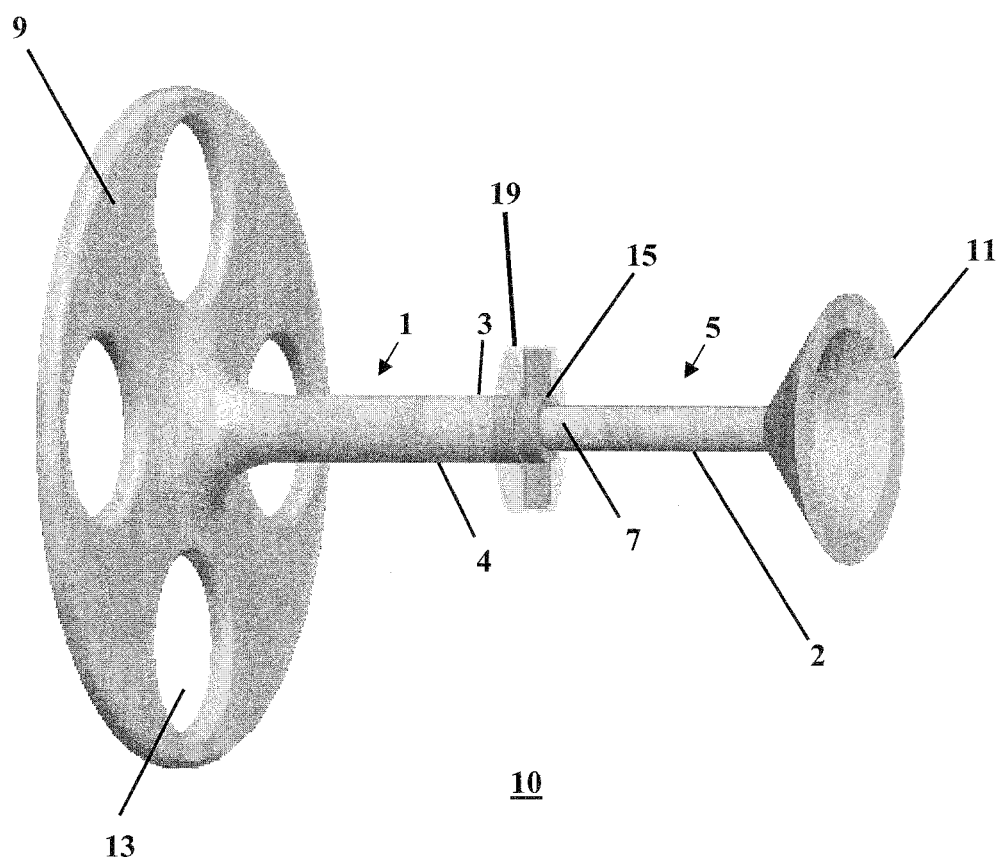
FIG. 1 shows an adjustable middle ear prosthesis in accordance with an embodiment of the subject invention, with a casing for hermetically sealing the clamps.
Figure 2:
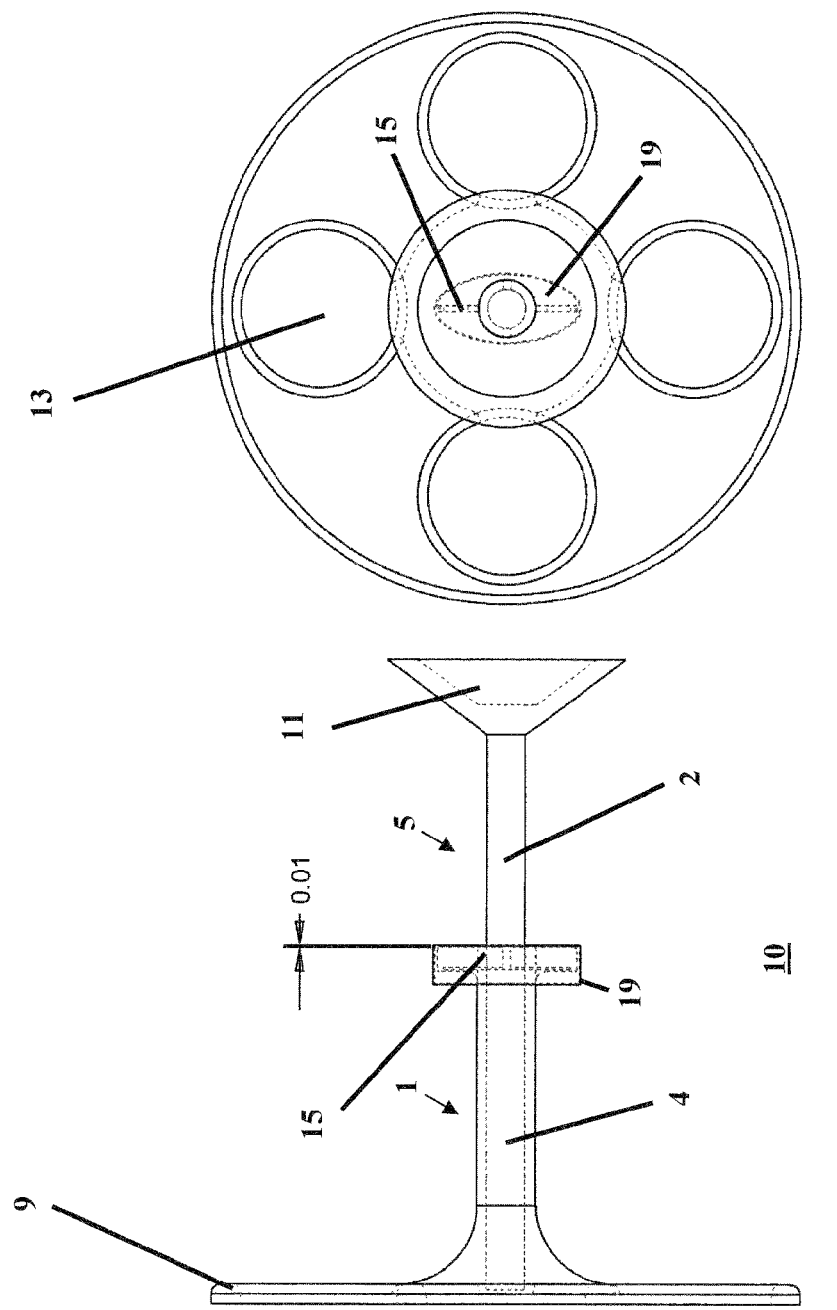
FIG. 2 shows a longitudinal cross-section and an end view of an adjustable middle ear prosthesis with a casing, in accordance with an embodiment of the subject invention.

Referring to FIGS. 1 and 2, in a specific embodiment, a middle ear prosthesis can have a first element 1 and second element 5, which are slidably connected to each other. The embodiment shown in FIGS. 1 and 2 slidably connect in a telescoping manner. The embodiment shown in FIG. 1 incorporated a first interconnecting end and a second interconnecting end that connected in a telescoping manner. The first element can have an outer cylinder 4 with an approximately cylindrical head 9 and an inner cylinder 2 with an approximately conical foot 11. In specific embodiments, the head 9 can be broad and flat, and in a further specific embodiment can have a substantially elliptical transverse cross-section. The head 9 can have other shapes such as elliptical. When the prosthesis is implanted in a patient, the head 9 of the outer cylinder can rest on the malleus or tympanic membrane and the foot 11 of the inner cylinder can rest on the stapes capitulum or footplate. Examples of the outer cylinder and the inner cylinder are shown in more detail in FIGS. 3 and 5, respectively. Though dimensions are listed in FIGS. 2-5, these are only for one specific embodiment, and embodiments of the present invention are not limited thereto. In an alternative embodiment, the outer cylinder can have the approximately conical foot 11 and the inner cylinder can have the approximately cylindrical head 9. Although circular cross-sections are shown in FIGS. 1-5 for the interconnecting ends of the first and second elements, other cross-sectional shapes can be utilized. Examples of other cross-sectional shapes that can be used for the interconnecting ends of the first and second elements include square, rectangular, hexagonal, polygonal, or other irregular shapes.

Figure 3:
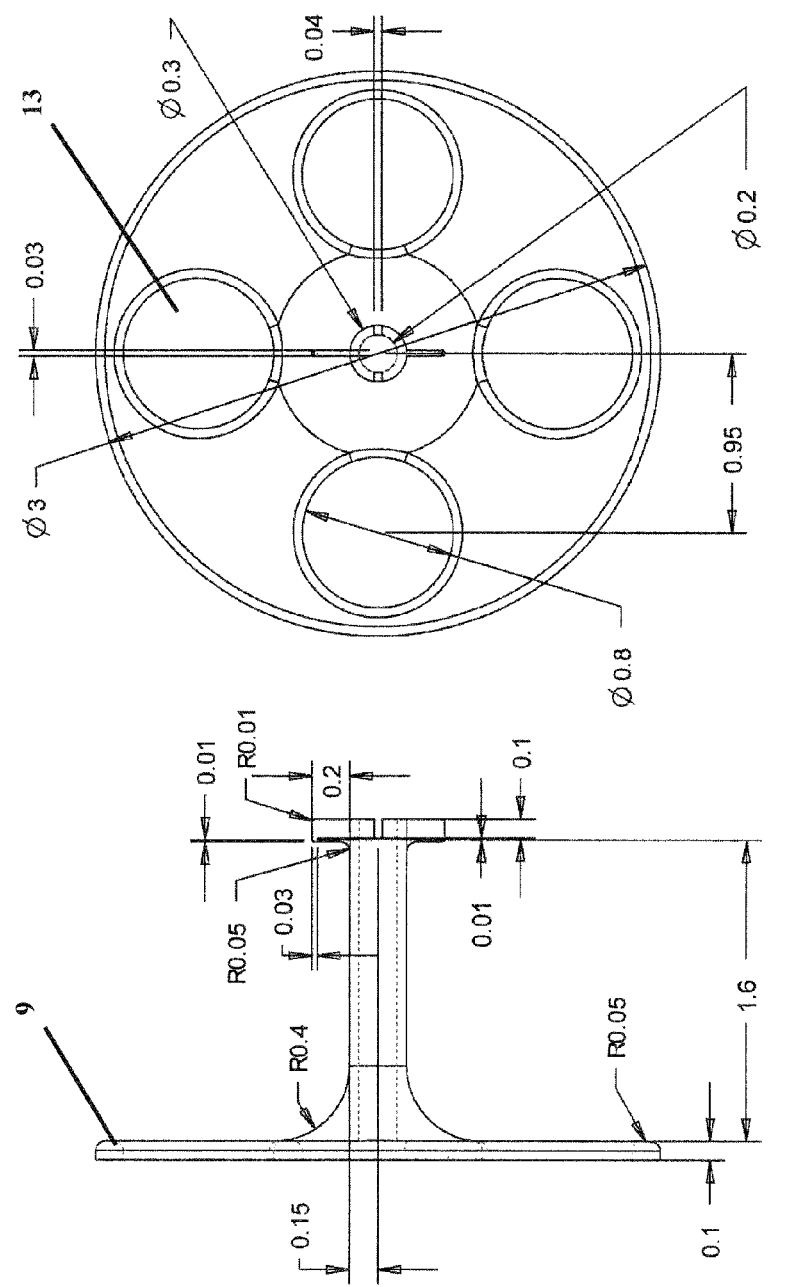
FIG. 3 shows a longitudinal cross-section and an end view of an element of a prosthesis having an outer cylinder for receiving an inner cylinder of another element, and a circular head, in accordance with an embodiment of the invention.
Figure 17:
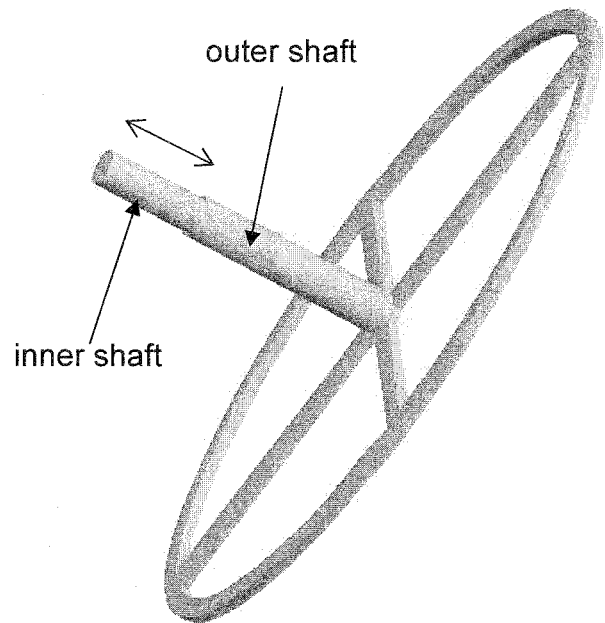
FIG. 17 shows a solid model of an adjustable length prosthesis.

The approximately circular or elliptical head 9 of the outer cylinder can have one or more apertures 13, as shown in the Figures. The apertures can enhance the attachment of the circular head 9 to the malleus bone, or other middle bone, via scar tissue. For example, the head 9 of the outer cylinder can have four apertures 13 equally spaced radially around the head (as shown in FIG. 3). In alternative embodiments, the head 9 of the outer cylinder can have more or less than four apertures 13 or can have no apertures 13 at all. Still another alternative embodiment, the head 9 of the outer cylinder can be a circular rim connected to the outer cylinder 4 by radial spokes as shown in FIG. 17.

Figure 6:
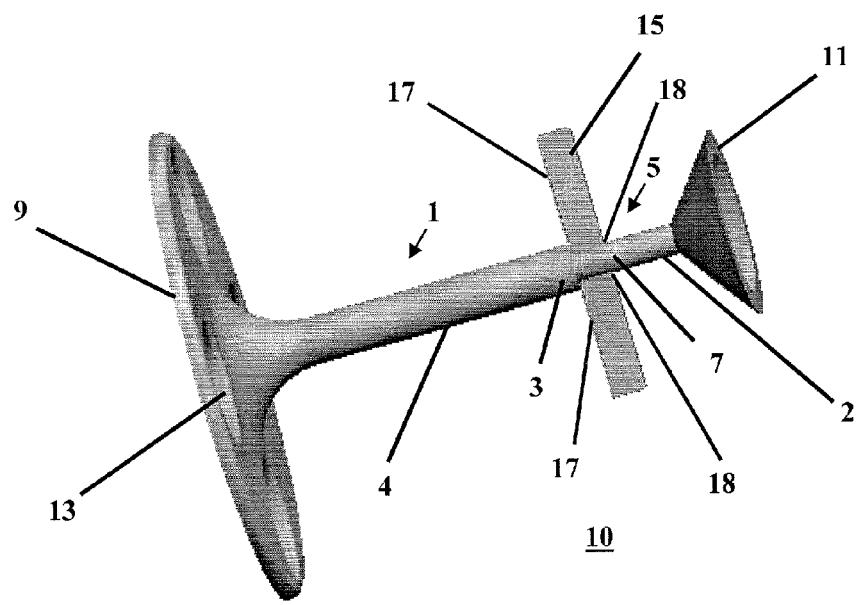
FIG. 6 shows a perspective view of an embodiment having clamps on an inner cylinder.
Figure 7:
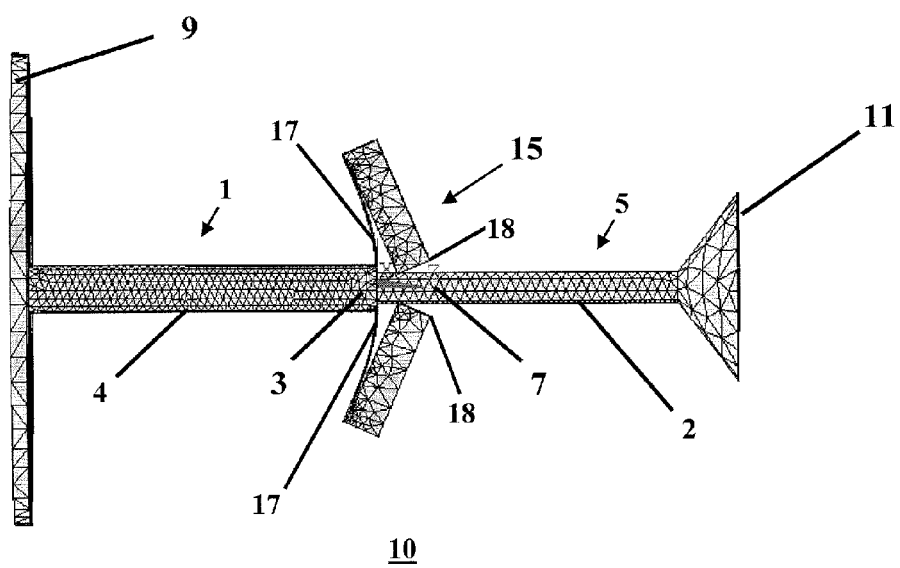
FIG. 7 shows exaggerated bending of the clamps and releasing of the inner cylinder.
Figure 9:
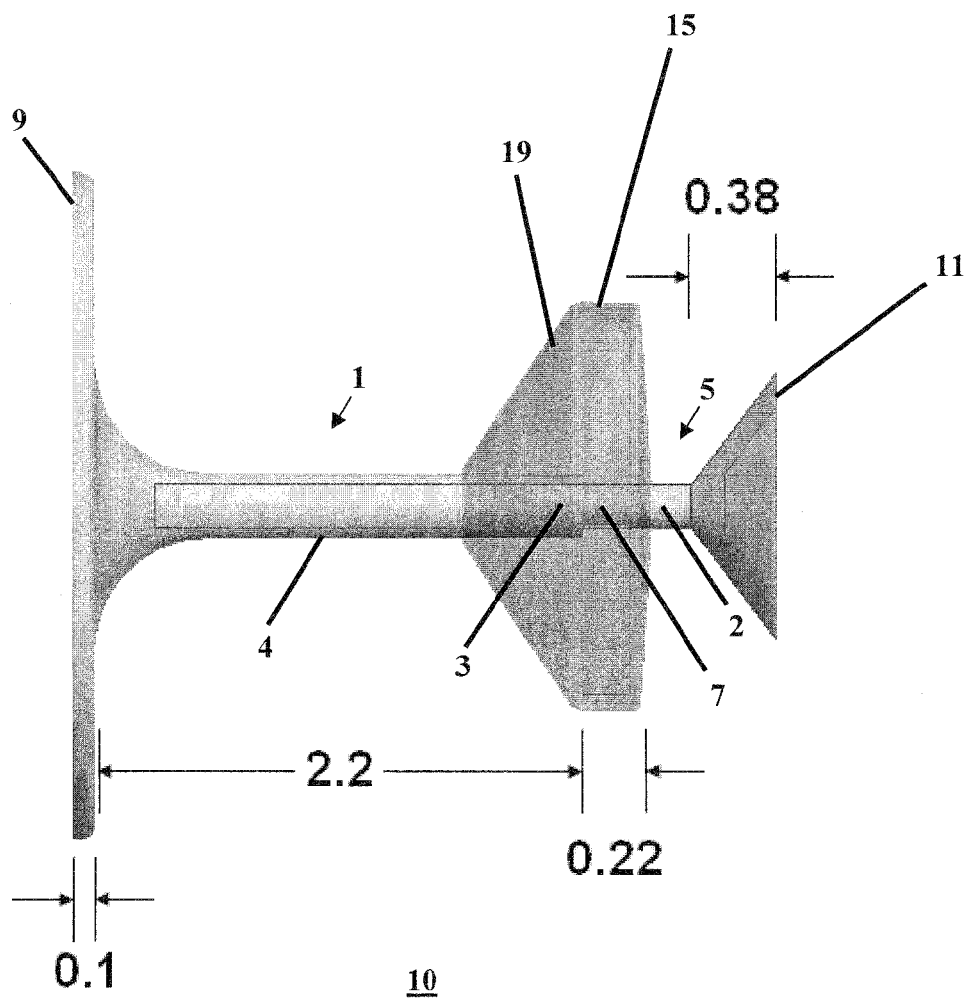
FIG. 9 shows dimensions of a middle ear prosthesis according to an embodiment of the present invention.
Figure 10:
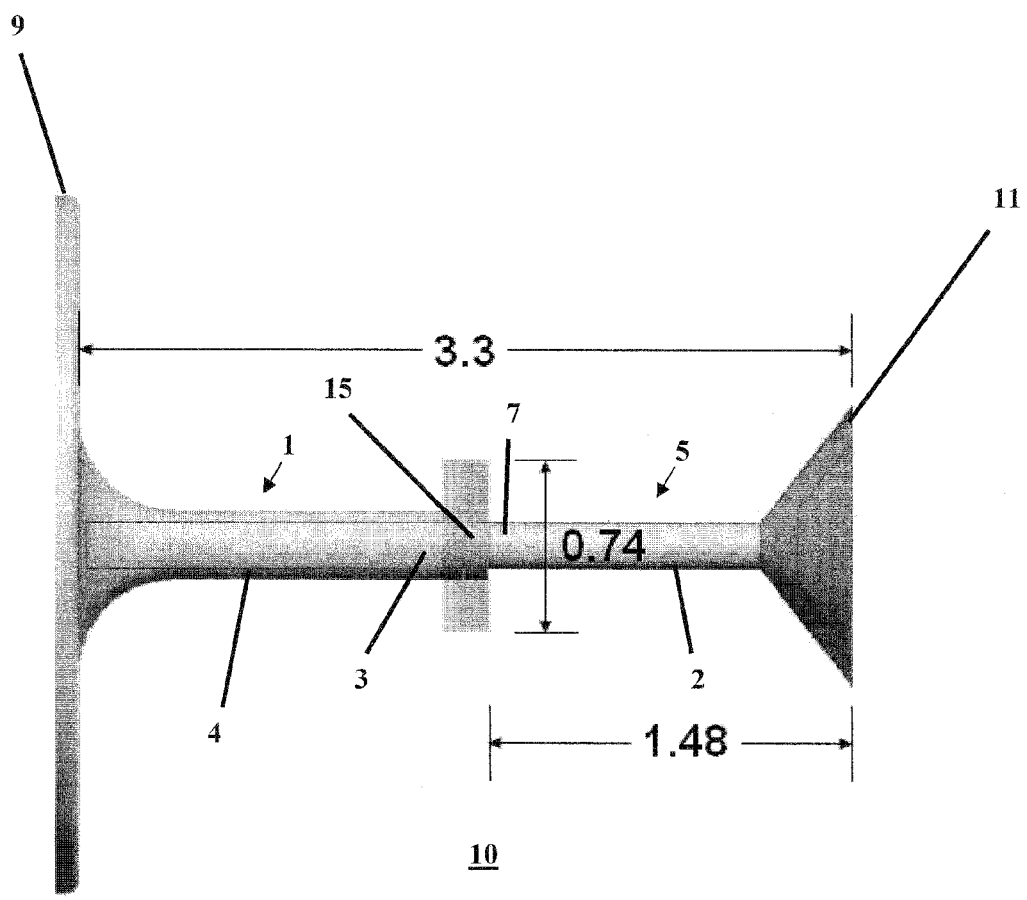
FIG. 10 shows dimensions of a middle ear prosthesis according to an embodiment of the present invention.

The second interconnecting end 7 of the second element 5 can be inserted into the first interconnecting end 3 of the first element 1. In the embodiment shown in FIG. 1, the inner cylinder 2 can be inserted into the outer cylinder 4, and the middle ear prosthesis can have a clamp 15 to hold the inner cylinder in place with respect to the outer cylinder or allow the inner cylinder to slide longitudinally into or out of the outer cylinder. The clamp 15 can be connected to either the inner cylinder or the outer cylinder. For example, referring to FIGS. 3, 6, and 7, as shown in FIG. 6, a compliant portion 17 of the clamp can be affixed to, and/or integrated with, the outer cylinder such that the compliant part 17 pushes the clamp 15 against the inner cylinder when the inner cylinder is inserted into the outer cylinder and the compliant part is released such that the clamp head 18 contacts the inner cylinder and the complaint part 17 holds the clamp head against the outer surface of the inner cylinder. Referring again to FIG. 7, when a force is applied to the clamp 15, the compliant portion 17 can bend, thereby allowing the inner cylinder to slide longitudinally further into or out of the outer cylinder. In actual use, the compliant part 17 will not bend as far as FIG. 7 shows in which the bending displacement is exaggerated for visual clarity. The radial length and width of the clamps need not be the dimensions used to illustrate in FIGS. 33 and 9 for example. The value of the force required to bend the compliant beam can be dependent on the radial length of the clamp.

In another embodiment (not shown in the Figures), the clamp 15 can be affixed to, or integrated with, the inner cylinder and can grip the outer cylinder. The compliant part 17 for a clamp positioned on the inner cylinder can function as described above for embodiments in which the clamp 15 is affixed to, or integrated with, the outer cylinder. However, having the clamp position on the inner cylinder can restrict the range of change in length possible as the outer cylinder can run into the clamp and/or pull far enough away to be out of range of the clamp 18, unless a portion of the outer cylinder is cut away to allow the clamp to pass through the outer cylinder.

Figure 4:
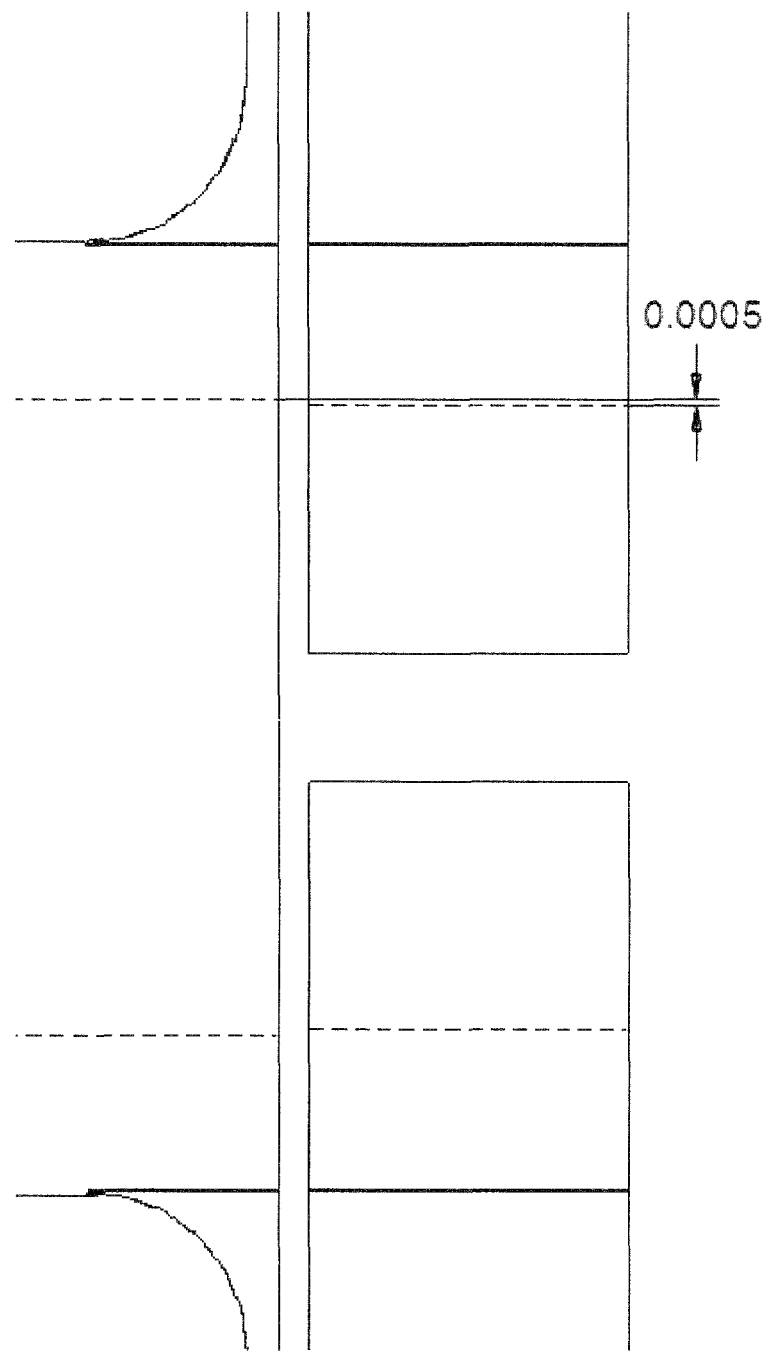
FIG. 4 shows a close-up of a longitudinal cross-section of the outer cylinder and clamp from FIG. 3, depicting the difference in the diameter of the inner surface of the clamp and the inner diameter of the outer cylinder.
Figure 5:
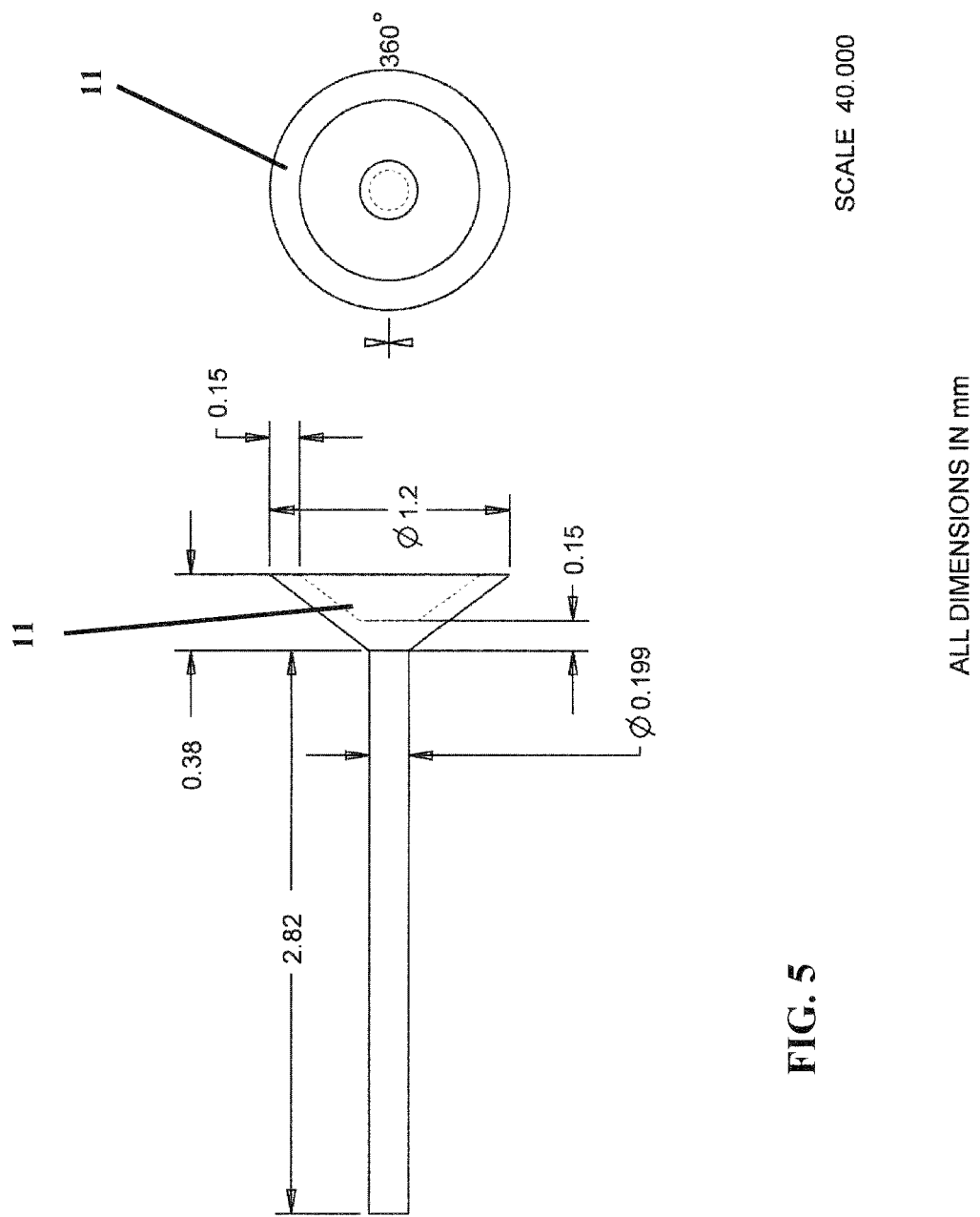
FIG. 5 shows a longitudinal cross-section and an end view of a second element that is complimentary to the element of FIG. 3 and has an inner cylinder with a conical end.

The clamp 15 can incorporate one or more clamp elements, or pieces, with a clamp head 18 to inhibit unwanted sliding between the cylinders. Preferably, the clamp 15 has at least two clamp heads 18 with associated compliant parts 17. Referring again to FIG. 7, in one embodiment, the clamp 15 has exactly two clamp heads 18 on opposite sides (radially) of the inner cylinder. Preferably, the clamp heads are positioned such that a net-zero torque is applied to the interconnecting end of the second element to reduce binding between the interconnecting ends. In an embodiment with compliant parts having the same force per angle deflection the clamp heads can be positioned symmetrically around the first interconnecting end. Each clamp head can have a distal end that can contact the inner cylinder and a proximal end away from the inner cylinder (as shown in FIG. 7) that is affixed to, or integrated with, the compliant part 17. The diameter of the inner surface of the clamp can be slightly smaller (on the order of 0.001 mm as shown in FIG. 4 which shows the radial difference as 0.0005 mm), on at least a portion of the clamp head, than the outer diameter of the inner cylinder and the inner diameter of the outer cylinder. In an embodiment, this difference in diameter can be less than 0.002 mm. In a further embodiment, this diameter is less than 0.001 mm. In further embodiments, this difference can be in the range 0.0005 mm to 0.001 mm, and in another embodiment, this difference in diameter can be less than 0.0005 mm. This will result in the clamping of the inner cylinder when the clamp is released so as to be in the equilibrium position, where when in the equilibrium position, the compliant part applies a force to push the clamp head into the inner cylinder.

The clamp head can have a variety of shapes that the compliant part causes at least a portion of the clamp head into contact with the outer surface of the interconnecting end of the second element, such as an outer surface of an inner cylinder, in order to create enough friction to hold the first element and second element in place with respect to each other. In a preferred embodiment, the radius of curvature of the clamp head is the same as the radius of curvature of the outer surface of the inner cylinder when the clamp head contacts the inner cylinder, so as to create a large amount of surface area contact between the clamp head and the inner cylinder. In another embodiment, the clamp head has a radius of curvature, form by boring into the first piece, which is larger than the radius of curvature of the outer surface of the inner circle, where both are circular-shaped radius of curvatures.

Figure 11:
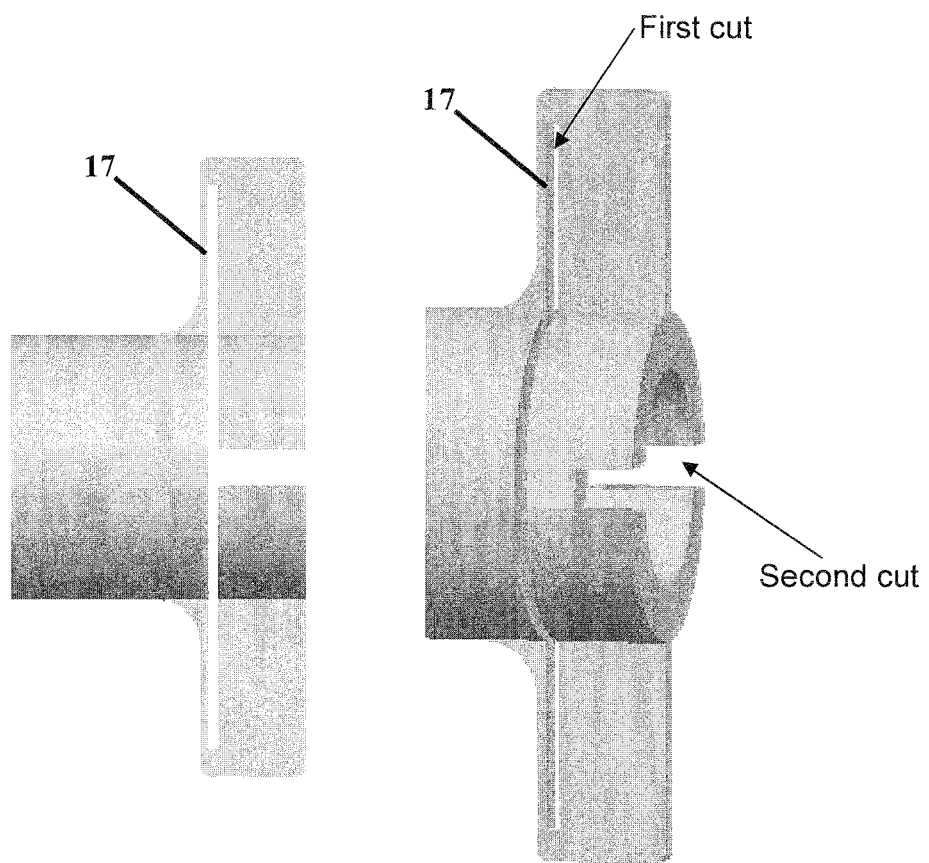
FIG. 11 shows cuts for a manufacturing process of a middle ear prosthesis according to an embodiment of the present invention.
Figure 12:
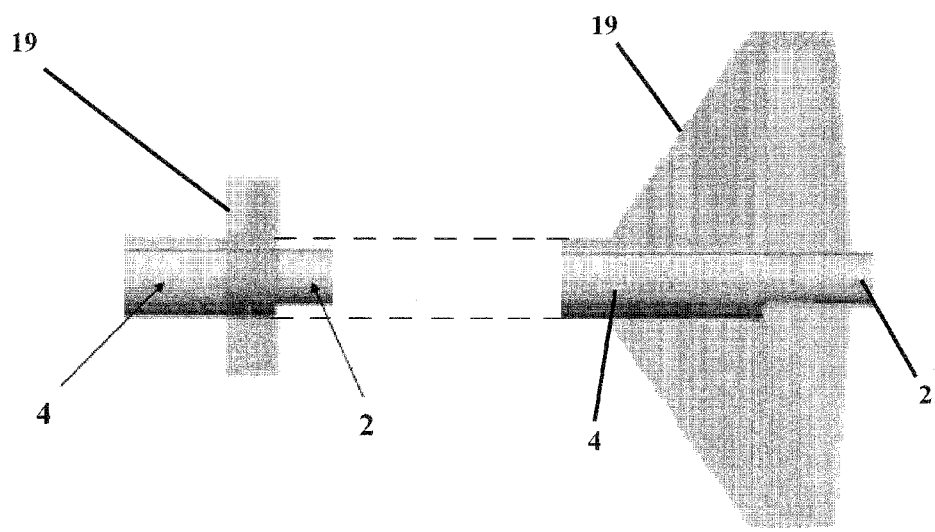
FIG. 12 shows the clamps and casing for two embodiments of a middle ear prosthesis in accordance with the subject invention, with the embodiment on the left having shorter clamp pieces than the embodiment on the right.
Figure 13:
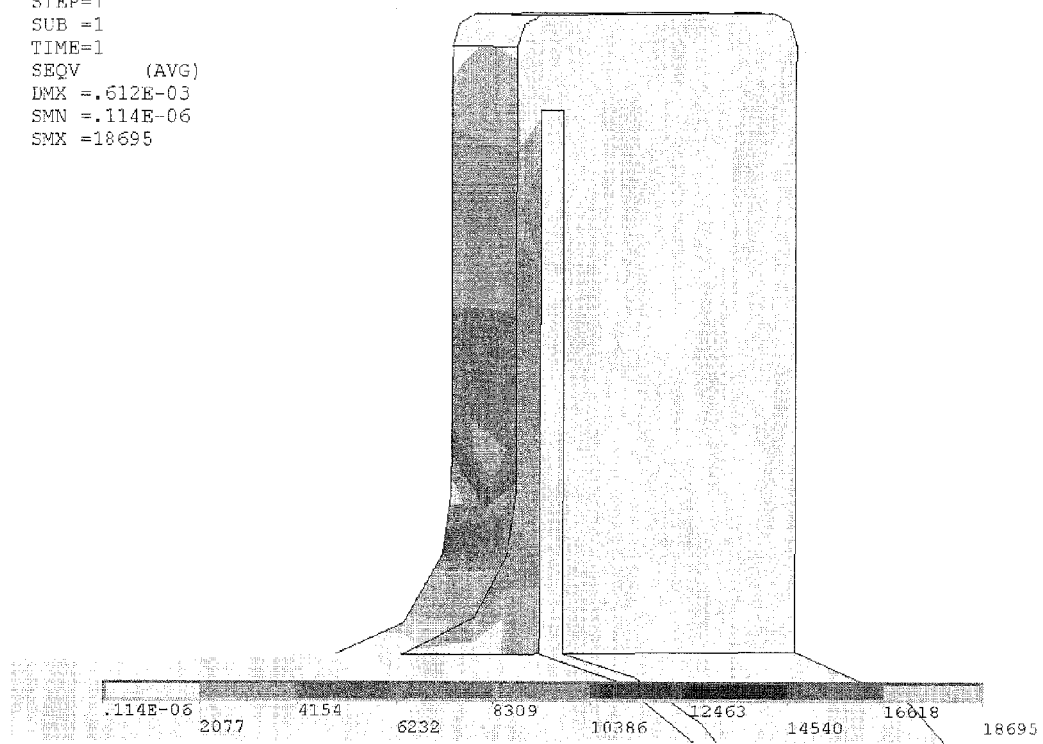
FIG. 13 shows a stress distribution along the compliant part a clamp in accordance with an embodiment of the invention.

The small size of the prosthesis poses a challenge for the manufacturing process. The design of the embodiment shown in FIG. 1 allows for an efficient manufacturing process. The outer cylinder and the clamps can be manufactured from a single solid piece of material with the clamps being created by cutting twice through this single piece and the outer cylinder created by drilling into the piece. In a specific embodiment, the clamp is integral with the outer cylinder of the first element. The breadth of the compliant part can be equal to the breadth of the clamp or can have a different breadth. Having the same breadth can help in separating the compliant beam from the clamps by just cutting along the length of the clamps. Then a second cut can be made across the piece to obtain the two separate clamp heads (as shown in FIG. 11). The piece can then be drilled to make a bore hole throughout the clamp head with the diameter of the hole equal to the diameter of the inner surface of the clamp. The clamp heads can then be pulled out of the way and a bore drilled into the outer cylinder portion of the single piece. The inner diameter of the outer cylinder is then drilled slightly larger than the diameter of the diameter of the inner surface of the clamp, so that the inner diameter of the outer cylinder is larger than the outer diameter of the inner cylinder and the inner diameter of the distal ends of the clamp heads is smaller than the other diameter of the inner cylinder. The clamps can be bent out of the way by applying a force on the ends of the compliant parts and then the required inner diameter of the outer cylinder can be obtained by boring through just the outer cylinder. Another set of manufacturing steps can also be used to fabricate embodiments of the present invention where the limitations are those of the manufacturer's access to the state-of-the-art fabrication techniques and processes. One of the most important properties for a middle ear prosthesis is the ability to avoid any microbial growth. It has been observed by surgeons that if there is any gap between the components of a prosthesis, it may result in microbial growth, possibly leading to a clinical infection (i.e., manifest by pain, effusion, and extrusion). Thus, the tolerances for the gap between the components is preferably less than or equal to 1 micron, including the gap between the inner diameter of the outer cylinder and the outer diameter of the inner cylinder.

Figure 8:
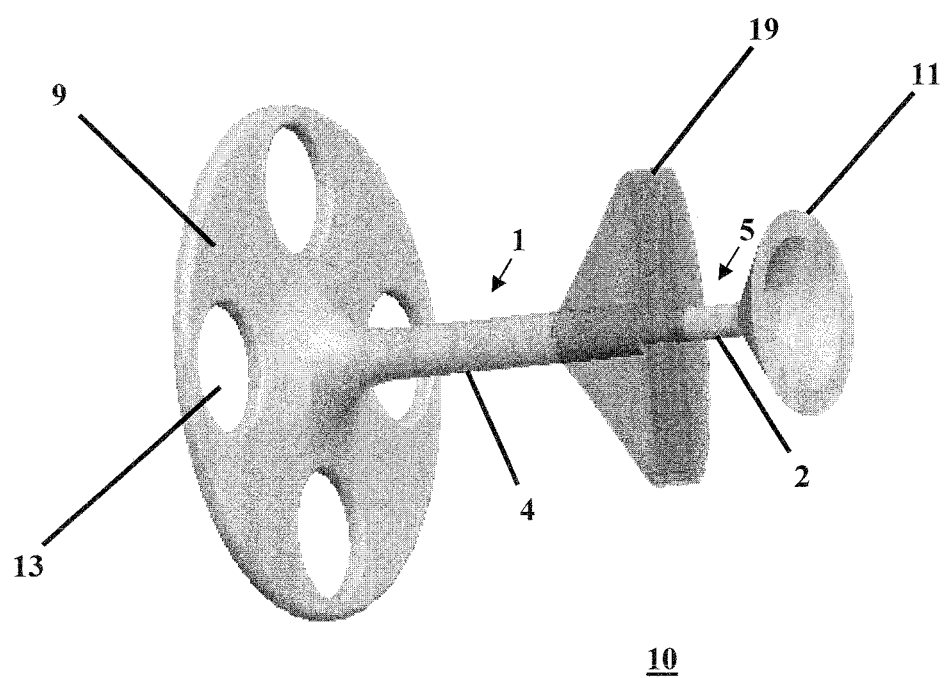
FIG. 8 shows a hermetically sealed casing around the clamps.

With respect to specific embodiments, the gap created when the clamp pieces move to allow longitudinal sliding of the inner cylinder may be large enough to lead to bacterial growth. To address this problem, an embodiment of the present invention can include a hermetically-sealed casing 19 around the clamp, as shown in FIG. 8. The seal can be fixed to the outer cylinder and completely cover both the clamps. The seal can either be tightly wrapped to the inner cylinder but allow sliding of the inner cylinder or can be fixed to the inner cylinder and not allow any relative motion. In a specific embodiment where the seal is fixed to the inner cylinder, it can be made of a flexible material that allows sliding of the inner cylinder into and out of the outer cylinder and thereby allow a change in the length of the prosthesis. The hermetically-sealed casing can be made of any suitable material known in the art, e.g., silicon rubber, epoxy resin, and advanced ceramic materials, and can have any suitable shape. For example, as shown in FIG. 8, the hermetically-sealed casing 19 can be approximately flat in a direction facing the foot of the inner cylinder and can extend parallel to the longitudinal axis of the cylinders and then taper down toward the outer cylinder.

Additionally, to prevent microbial growth on the surfaces, the parts can be textured in such a pattern as to inhibit bacteria growth or be coated with an antimicrobial material. In one embodiment, the surfaces have an antimicrobial texture. In another embodiment the surfaces are coated with an antimicrobial material.

The prosthesis can be made from any suitable material known in the art, such as titanium for the first and second contact ends, inner and outer cylinders and clamps, with a material that creates a force on the compliant part when exposed to a magnetic field positioned on the prosthesis. Titanium is one of most suitable materials for medical implants because of its biocompatibility and good material properties. It is corrosion resistant, has little effect on tissue morphology and does not produce any clinical conditions. Also, the hearing range of the human ear is 40-2000 Hz, which is approximately nine octaves. Tests have demonstrated that the mass of the implant will affect the optimum transmission frequency, with the lightest mass performing best. Titanium implants are light implants and thus produce good vibration transmission. Titanium implants also have good vibration properties (for proper sound transmission) and a high yield strength value in the order of 1200 MPa, thus, making titanium an ideal choice for the material.

Embodiments of the subject middle ear prosthesis are in the range of 2 mm to 7.5 mm (2 to 4.5 mm for PORPs and 3 to 7.5 mm for TORPs). Using a pair of telescopic cylinders, the size of the prosthesis can be varied when the inner cylinder is extended from the fully contracted state (when it is completely inside the outer cylinder) to the fully expanded state (when completely outside the outer cylinder). Thus, using these outer and inner cylinders, the size of the prosthesis can only be doubled (approximately). Also, because people heal differently, each prosthesis should be able to be adjusted to be longer or shorter by as much as 0.5 mm. In order to achieve this and to cover sizes ranging from 2 mm to 7.5 mm there can be four different sets of embodiments for the PORP and three different sets of embodiments for the TORP of the present invention. The first embodiment for the PORP can have a size varying from 1.8 to 2.9 mm, where 1.8 mm is the length of the unextended prosthesis and 2.9 mm is the length of the extended prosthesis. Similarly, the second embodiment for a PORP can have a size varying from 1.9 to 3.1 mm, the third embodiment for the PORP can have a size varying from 2.1 to 3.5 mm and the fourth embodiment for PORP can have a size varying from 2.5 to 4.3 mm. The first embodiment for the TORP can have a size varying from 3.3 to 4.8 mm, the second embodiment for the TORP can have a size varying from 3.8 to 5.8 mm and the third embodiment for PORP can have a size varying from 4.8 to 7.8 mm.

The components of the middle ear prosthesis according to the various embodiments of the present invention can also be of varying sizes depending on the overall range of size of the prosthesis. In an embodiment, the outer cylinder can have a length of from about 1.41 mm to about 2.11 mm. In a further embodiment, the outer cylinder can have a length of from about 1.81 mm to about 3.31 mm. In yet a further embodiment, the outer cylinder can have a length of from about 1.51 mm to about 4.3 mm. In yet a further embodiment, the outer cylinder can have a length of about 1.71 mm. In yet a further embodiment, the outer cylinder can have a length of about 2.31 mm.

In an embodiment, the inner cylinder can have a length of from about 1.7 mm to about 2.4 mm. In a further embodiment, the inner cylinder can have a length of from 3.2 mm to about 4.7 mm. In yet a further embodiment, the inner cylinder can have a length of about 1.8 mm. In yet a further embodiment, the inner cylinder can have a length of about 2.0 mm. In yet a further embodiment, the inner cylinder can have a length of about 3.7 mm. In an embodiment, the length from the distal end of one clamp piece to the distal end of the opposite clamp piece can be from about 0.7. In a further embodiment, the length from the distal end of one clamp piece to the distal end of the opposite clamp piece can be about 2.3. In yet a further embodiment, the length from the distal end of one clamp piece to the distal end of the opposite clamp piece in addition to the thickness of the casing can be about 0.74 mm.

In an embodiment, the side-view thickness of the approximately circular head 9 of the outer cylinder can be less than about 0.1 mm. In a further embodiment, the side-view thickness of the approximately circular head 9 of the outer cylinder can be less than about 1 mm. In yet a further embodiment, the side-view thickness of the approximately circular head 9 of the outer cylinder can be less than about 0.2 mm. In yet a further embodiment, the side-view thickness of the approximately circular head 9 of the outer cylinder can be about 0.1 mm.

In an embodiment, the side-view thickness of the approximately conical foot 11 of the inner cylinder can be less than about 0.3 mm. In a further embodiment, the side-view thickness of the approximately conical foot 11 of the inner cylinder can be less than about 0.5 mm. In yet a further embodiment, the side-view thickness of the approximately conical foot 11 of the inner cylinder can be about 0.38 mm. In an embodiment, the diameter of the approximately circular head 9 of the outer cylinder can be less from about 3 mm to about 5 mm. In a further embodiment, the diameter of the approximately circular head 9 of the outer cylinder can be less from about 1 mm to about 4 mm. In yet a further embodiment, the diameter of the approximately circular head 9 of the outer cylinder can be 3 mm.

In an embodiment, the diameter of the approximately conical foot 11 of the inner cylinder can be less from about 0.6 mm to about 1.5 mm. In a further embodiment, the diameter of the approximately conical foot 11 of the inner cylinder from about 1 mm to about 2 mm. In yet a further embodiment, the diameter of the approximately conical foot 11 of the inner cylinder can be 1.2 mm.

The middle ear prosthesis can be adjusted after placement in the middle ear, by causing the clamp 15 to bend in situ, without the need for surgery to first remove the prosthesis in order to have direct contact with the clamp 15. In one embodiment, to adjust the length of the prosthesis, a force can be applied to the distal ends of the clamp pieces to make the compliant portion 17 of the clamp 15 bend, thereby allowing the inner cylinder to slide longitudinally. For example, the distal end of each clamp piece can have a magnetic material and/or a magnet, and an external magnetic field can be applied to cause the clamp 15 to bend. The magnetic field can be applied by, for example, an electromagnet outside the ear. The magnitude of the forces can be controlled by controlling the voltage applied on the electromagnet. The magnetic material and/or magnets can be positioned on the clamp such that when a magnetic field is applied the magnetic field creates a force on the clamp so as to pull the clamp away from the inner cylinder such that the inner cylinder can slide with respect to the outer cylinder. In specific embodiments, the magnetic material and/or magnet can be positioned along the compliant parts 17, and preferably the distal end of the compliant part 17 to create the maximum torques and/or on the clamp head 18, preferably at the proximal end on the portion prior to the end of the first cut such that the force tends to pull the clamp head away from the inner cylinder rather than push the clamp head toward the inner cylinder.

Figure 14C:
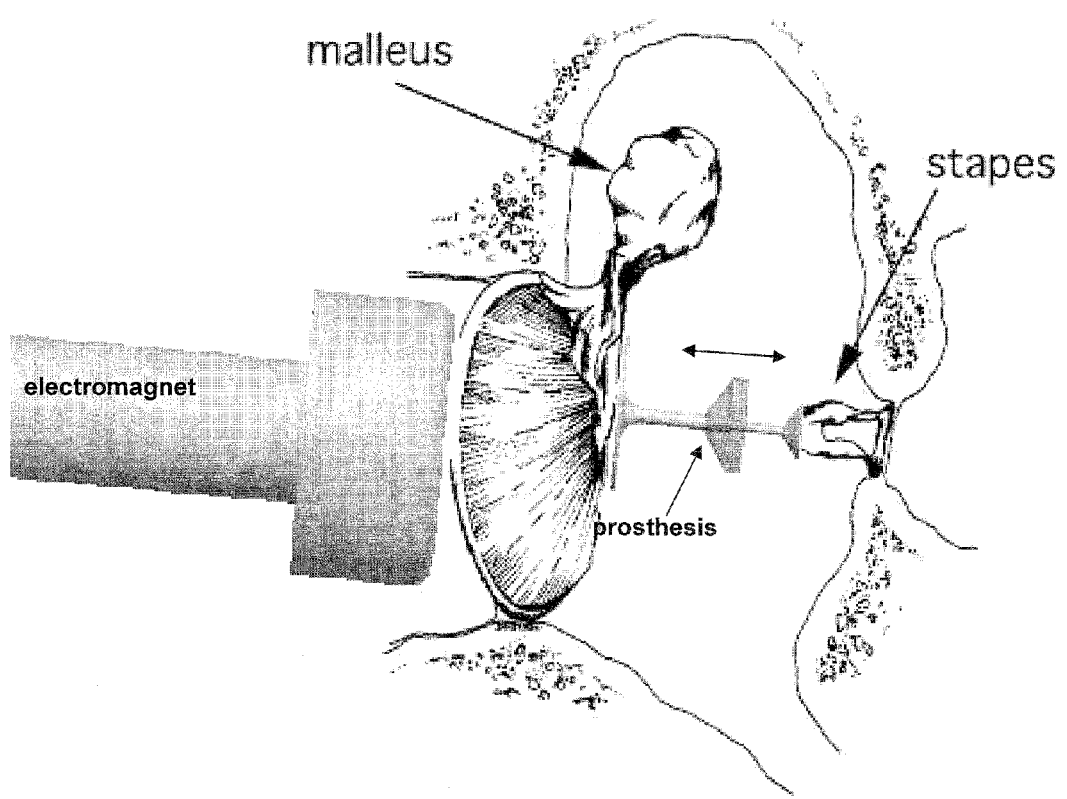
FIG. 14C shows the use of an electromagnet to adjust the embodiment of the prosthesis shown in FIG. 14B.
Figure 14D:
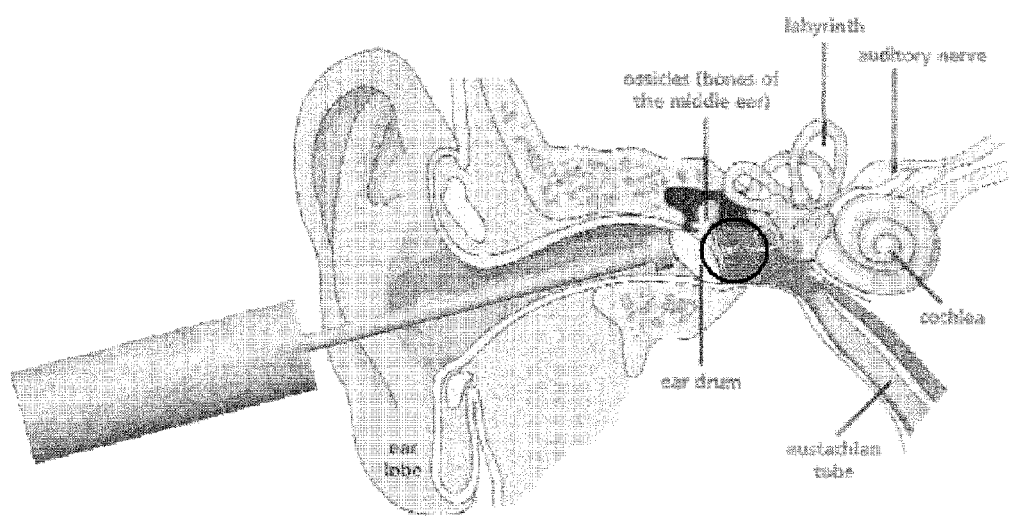
FIG. 14D shows the use of the electromagnet as shown in FIG. 14C, from a larger perspective, where the electromagnetic support is placed against an ear drum, where the electromagnet can be used to actuate a clamp in accordance with the embodiment.

The external forces applied on the prosthesis, by the electromagnet on the magnets on the clamp, might tend to push the entire device against the malleus and the eardrum instead of just bending the compliant part. To counter this, a support can be provided at the end of the electromagnet that can be placed against the eardrum. The support can impede the displacement of the whole device such that the compliant part bends without transformation of the entire prosthesis, as shown in FIGS. 14B-14C. An alternate method of force activation could be via an embodiment with an induction coil behind the ear. The induction coil can be driven to produce a magnet field to actuate the clamp.

Embodiments of the subject prosthesis can have the length of the prosthesis adjusted by actions of a caregiver and apparatus external to the middle ear, while the prosthesis is in situ in the middle ear. This means that if, after the patient has healed from the initial surgery of implanting the prosthesis, the patient finds that due to post-surgical variations occurring within the middle ear the initial prosthesis length is no longer correct the length of the prosthesis can be adjusted without additional surgery. With a prosthesis, according to embodiments of the present invention, a physician can make in situ length adjustments of the prosthesis as needed. That is, the physician can have the ability to fine tune the prosthesis to correct and improve a patient's hearing without additional surgeries. With respect to specific embodiments, the in situ length adjustment can be made without insertion of tools into the middle ear.

The benefits of externally adjustable prosthesis are multifold: first, it minimizes risk involved in any additional surgeries. Secondly, it will improve physician's efficiency by decreasing time spent with each patient. Another benefit is that by having a prosthesis that can be both shortened and lengthened the prosthesis may not need to be discarded if it is too short.

The following steps can be followed during the first operation to insert the prosthesis in the patient. The patient's ear is opened up and the prosthesis of the appropriate size is inserted and positioned onto the malleus and stapes. Then the electromagnet and the support are placed against the eardrum. The electromagnet is magnetized by slowly increasing the voltage supplied. At a certain value of the voltage, the angular deflection of the clamp will reach the required value for release (the value of this voltage [$v_0$] can be noted for future readjustment). The voltage supplied is maintained at this value and the inner cylinder is manually slid using tweezers to get the desired length for the prosthesis. The desired length can be determined keeping in mind that the best vibration transmission is achieved by a shorter prosthesis, which results in lower tension. The voltage supplied to the electromagnet can then be slowly reduced to zero so that the compliant part returns to its equilibrium position and clamps the inner cylinder. The ear drum support and the electromagnet can then be gently removed and the ear closed up.

The following non-invasive and external procedure can be followed for future re-adjustment of the length of the prosthesis, if and when it is required. The electromagnet and the support are carefully placed against the eardrum. The electromagnet is then magnetized by slowly increasing the voltage to the previously noted value $v_0$ (or to a slightly higher value). The magnetic forces created will release the clamps allowing the inner cylinder to slide. The voltage to the electromagnet is maintained at this value and the length of the prosthesis is adjusted to the required length using procedures known in the art, such as using micro tweezers to directly pull or push on the malleus or just pulling or pushing on the ear drum to cause sliding between the cylinders. The voltage supplied is then slowly reduced to zero so that the compliant part returns to its equilibrium position and clamps the inner cylinder. The electromagnet and the support are then carefully removed.

Embodiments of the prosthesis of the present invention have been analyzed by doing stress analysis of the prosthesis using ANSYS. The forces involved in causing the bending of the clamps are in the order of 0.25 mN to 5 mN (depending on the radial length and width of the clamps). The stresses developing on the compliant part upon the application of these forces are in the order of 20 MPa, which is much less than the yield strength of the materials that can be used for the prosthesis (for e.g., Titanium). Also, the pressure exerted by the circular head 9 on the malleus due to these forces will be in the order of 70 Pa. (considering a diameter of 3 mm for the circular head). Additionally, the prosthesis is not likely to have fatigue failure. Specific embodiments can use materials to reduce the risk of injury when exposed to magnetic fields of an MRI scanner, where titanium is a material that can be used. Further embodiments of the present invention are discussed below.

Example 1

For an embodiment having clamps 15 that keep the inner cylinder from sliding, a bistable mechanism can be used. A bistable mechanism has two stable positions and shifts from one stable position to another upon application of a small force. One stable position acts as a clamp and prevents the inner cylinder from sliding. A second stable position allows the inner cylinder to slide. Upon application of a magnetic field, the magnet on the clamp is pulled and upon the application of this force, the bistable mechanism shifts to the second stable position, thus releasing the inner cylinder. Once the inner cylinder is released, the length of the prosthesis can be changed. Once the desired length is obtained, the magnetic field can be reversed in polarity creating an opposing force on the magnet, and thus shifting the bistable mechanism to the first stable position so as to clamp the inner cylinder.

Example 2

Figure 27:
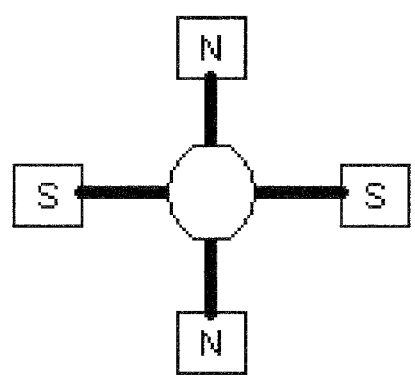
FIG. 27 shows a combination of magnets on a clamp having four clamping elements according to an embodiment of the present invention.

A specific embodiment can have 4 clamps 15 with a permanent magnet on each clamp. The clamps 15 and magnets can have the orientation as shown in FIG. 27. In this way, the inner cylinder is not released by a normal magnetic field because if one pair of clamps 15 is attracted by the field, the opposite pair is repelled. Rather the length can be changed by introducing a special adjusting device which has the exact opposite orientation to that of the clamps 15. Once the clamps 15 are released, the inner cylinder is free to be adjusted.

Example 3

Figure 28:
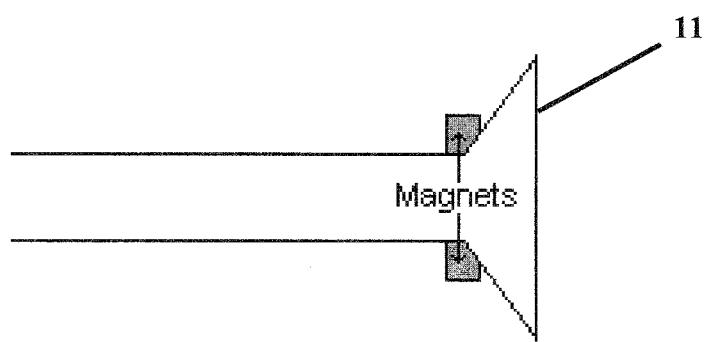
FIG. 28 shows permanent magnets on the edge of the cone of the inner cylinder according to an embodiment of the present invention.

This example describes an approach in adjusting the length of the prosthesis without having to pull or push the ear drum (as shown in FIG. 28).

Case 1: To increase the length, the polarity of the magnetic field of the electromagnet is maintained such that it is same as that of the permanent magnets on the base of the cone. When the magnetic material is pulled resulting in the bending of the compliant part 17, the inner cylinder is released from the clamps 15. Now, due to the repulsive forces between the permanent magnets on the inner cylinder and the external electromagnet, the inner cylinder is pushed farther away from the outer cylinder thus increasing the length of the prosthesis.

Case 2: To decrease the length, the polarity of the magnetic field of the electromagnet is maintained such that it is opposite to that of the permanent magnets on the base of the cone. The attractive forces in this case will pull the inner cylinder further into to the outer cylinder thus decreasing the prosthesis length.

Example 4

Figure 29:
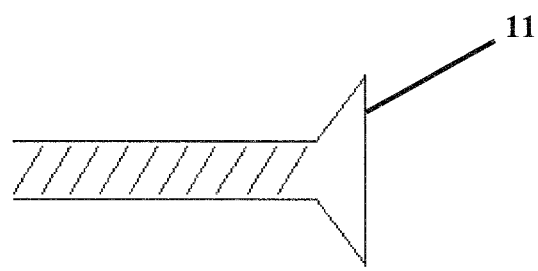
FIG. 29 shows a screw drive mechanism with threading on the outer and inner cylinders according to an embodiment of the present invention.

The circular head 9 of the outer cylinder has permanent magnets on them with the inner cylinder fitted into the threading of the outer cylinder. FIG. 29 shows a threaded inner cylinder. To change the length of the prosthesis, the electromagnet is introduced with opposite polarity and then rotated by an angle (which depends on the change in length required and the pitch of the screw). The permanent magnets will rotate by the same angle, thus rotating the outer cylinder, and accordingly, changing the overall length of the prosthesis. Similar to other embodiments, magnets of different polarities can also be located to cause the inner cylinder to rotate in opposite direction and/or to maintain zero force in the longitudinal direction of the prosthesis.

Example 5

Figure 30:
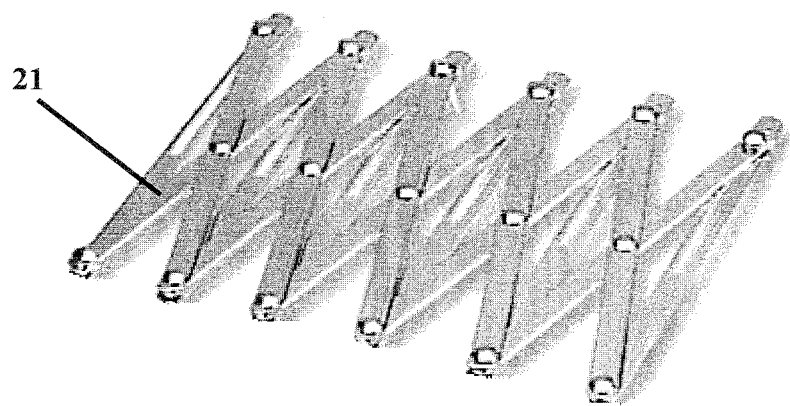
FIG. 30 shows an expandable lattice.

This embodiment uses a lattice structure 21, or a pantograph-type mechanism to expand the length of the prosthesis. Referring to FIG. 30, because the links can fold up the range of prosthesis length is very large. Both ends can be cemented in place in the initial surgery and the lattice 21 will expand or collapse accordingly as the patient heals.

Example 6

Figure 31:
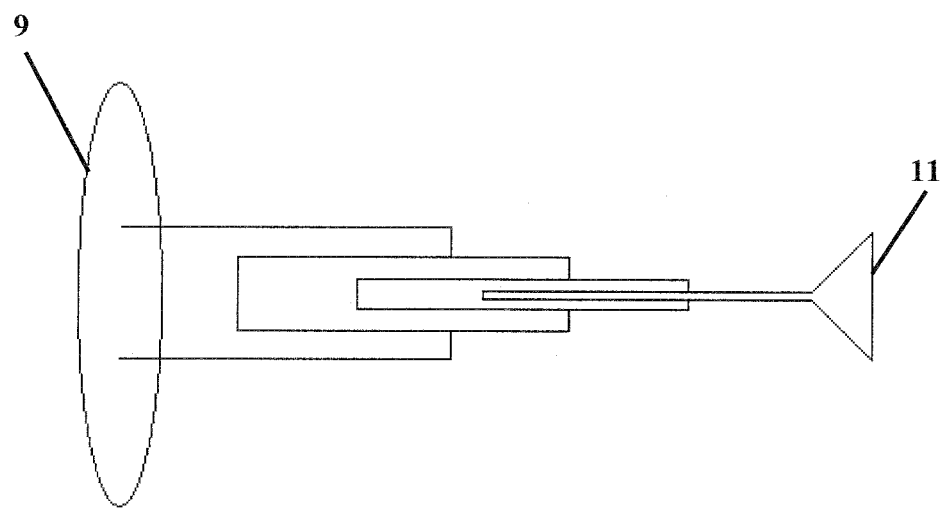
FIG. 31 shows multiple nested sliding cylinders according to an embodiment of the present invention.

This embodiment uses many sliding cylinders to achieve the full range of the TORPS and PORPS. Referring to FIG. 31, each cylinder can be created to have its displacement dependent on the displacement of another cylinder, thus giving the prosthesis one degree of freedom. The benefit of this design is that one size fits all and multiple sizes will not need to be manufactured.

Example 7

In an embodiment, the circular head 9 and the conical bell 11 are connected by a self-adjusting spring 23. During operation, it is compressed and the circular head 9 and the conical bell are properly placed in position and then the spring 23 is released. It would take the best possible length depending on the length between the circular head 9 and the conical bell 11 and adjust itself in case of any change that might occur in future, thus eliminating the need of adjusting the length for the second time.

Example 8

Figure 32:
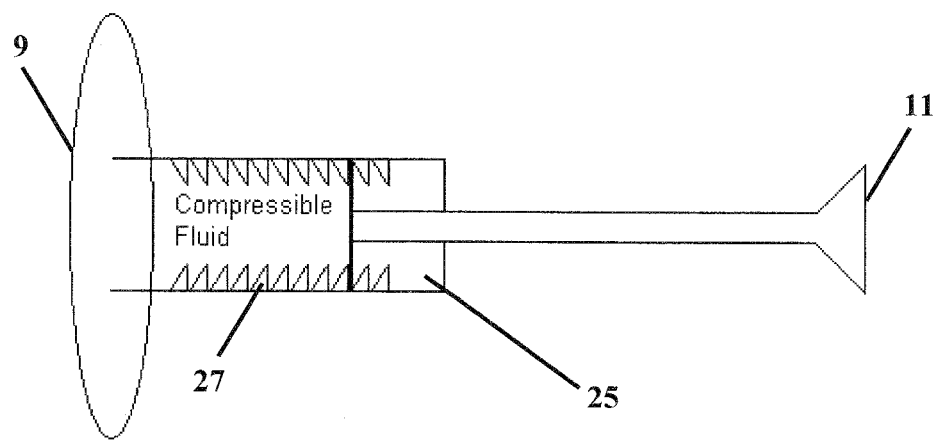
FIG. 32 shows pressurized fluid and a ratcheted setup according to an embodiment of the present invention.

An embodiment can use pressurized fluid 25 with a ratchet and valves, which allow a unidirectional change in length. Referring to FIG. 32, by decreasing external pressure the fluid in the prosthesis will expand causing the inner cylinder to move outward and expand the total length of the prosthesis. Once resized and pressure is brought back to atmospheric level, the fluid will try to pull the inner cylinder back. The unidirectional teeth 27 will impede the motion of the inner cylinder back into the outer cylinder thus keeping the length stable.

Example 9

Another embodiment has a method of measuring the tensions developing in the prosthesis during the healing process or due to deformations occurring in the middle ear over a long period of time.

Figure 26:
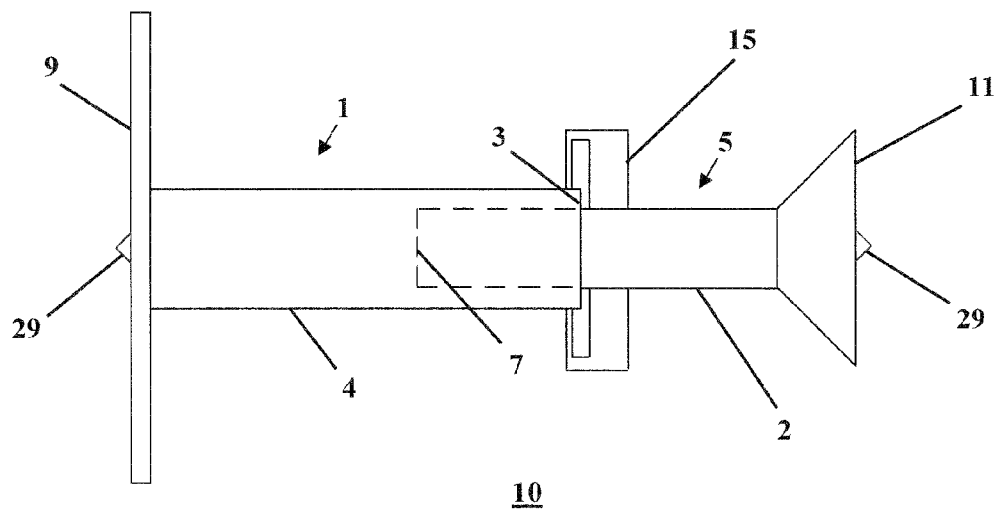
FIG. 26 shows a middle ear prosthesis having a clamp on an inner cylinder, according to an embodiment of the subject invention.

This embodiment can have a structure as described for other embodiments of the subject prosthesis and can incorporate one or more piezoelectric sensors, as shown on FIG. 26, on the head and/or the foot of the prosthesis. These sensors accurately measure the tensions acting on the prosthesis.

Due to the nature of the piezoelectric sensor, the tension acting on it results in deformation of the material and thus generates voltage. The value of the voltage generated depends on amount of tension forces acting on the prosthesis. The sensor can then be connected to, for example, a resistor circuit and a coil wrapped around a rod. This results in a current i flowing through the circuit (and the coil), which would be proportional to the voltage generated and thus would be proportional to the tension developed F.

$$i \propto F$$

This current flowing through the coil generates a magnetic field around the coil whose strength B would be proportional to the current flowing and thus proportional to the tension developed.

$$B \propto i$$

$$B \propto F$$

The strength of the magnetic field can be measured using a high precision magnetometer that can be placed close to the ear. From known relations, this value of B can be used to calculate the value of the tensions developed. If this calculated value is greater than the known allowable tensions on the prosthesis then the clamps have to be released to allow changes in the length of the prosthesis.

The clamps can be released by using the same approach (of electromagnetic support) used in the other described embodiments. Once the inner cylinder is unclamped, the length of the prosthesis can be changed and when a desired length is obtained the inner cylinder is clamped back. Afterward, since the tensions acting on the prosthesis would be lesser, the current i flowing through the coil and the value of B measured by the magnetometer will also be smaller. The corresponding tension can be adjusted to be less than the maximum allowable tension.

Example 10

Figure 33:
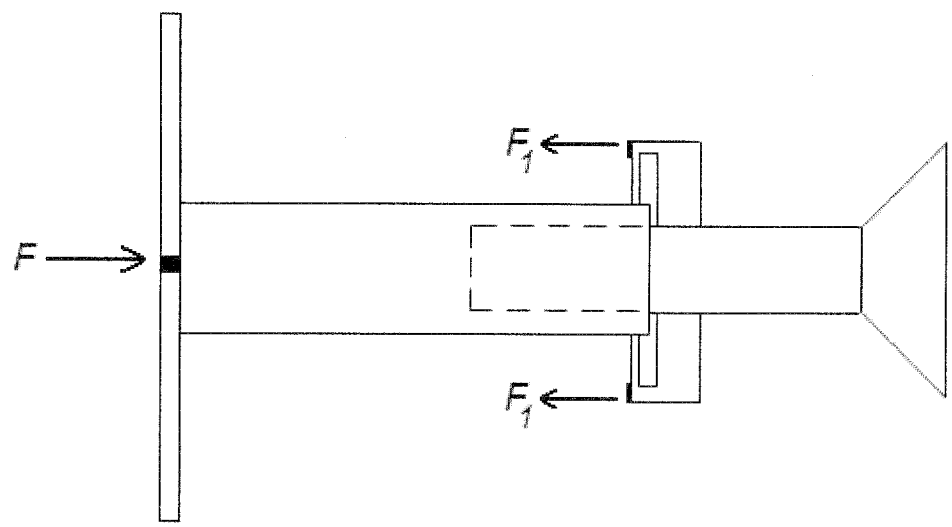
FIG. 33 shows additional magnets on the malleus head which will balance the net force on the prosthesis without the need of external support.

In a previous embodiments an electromagnetic support was used to prevent the entire prosthesis from moving during application of the magnetic field by pushing on the malleus and/or the ear drum upon the application of the magnetic forces. This force balance can instead be obtained by using extra magnets of same polarity as the magnetic field. In this embodiment, weak magnets are attached to the circular head of the outer cylinder (as shown in FIG. 33). When the external electromagnet is introduced externally, these weak magnets (of appropriate strength) are repelled by the magnetic forces (due to the same polarity) while the magnet/magnetic material on the compliant beam are attracted. This repulsion force can balance the net force on the prosthesis while the force on the compliant beam results in the bending of the clamps and release the inner cylinder. Once the length is adjusted, the electromagnet can be removed which results in the compliant beam returning to the equilibrium position and thus clamping the cylinder. The magnet on the head of the outer cylinder will be too weak to bend the compliant beam without the external field.

In a further embodiment, not shown in FIG. 33, a magnet can be placed at the proximal end of the compliant part such that a force equal but opposite to $F_1$ (see FIG. 33) is created at the proximal end of the compliant part (where $F_1$ is shown at distal end of compliant part) such that a net force of zero is exerted on the prosthesis when the magnetic field is applied to open the clamps. In this embodiment, a net-zero torque is applied on the prosthesis when the prosthesis is exposed to an external magnetic field such as in the vicinity of an MRI machine.

In a further embodiment, not shown in FIG. 33, a magnet can be placed at the proximal end of the compliant part such that a force equal but opposite to $F_1$ (see FIG. 33) is created at the proximal end of the compliant part (where $F_1$ is shown at distal end of compliant part) such that a net force of zero is exerted on the prosthesis when the magnetic field is applied to open the clamps. In this embodiment, a net-zero torque is applied on the prosthesis when the prosthesis is exposed to an external magnetic field such as in the vicinity of an MRI machine.

Example 11

Figure 15:
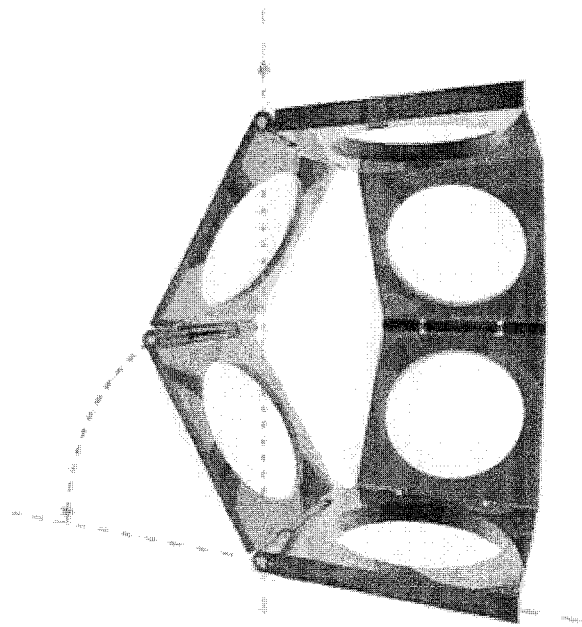
FIG. 15 shows a drawing illustrating a Sarrus linkage that can be incorporated with an embodiment of the invention.

One embodiment uses a Sarrus linkage, as shown in FIG. 15, to bridge the gap between the malleus and the stapes. One end of the Sarrus linkage can attach to the malleus while the other end attaches to the stapes. In another embodiment the malleus and stapes can be connected by a series of concatenated Sarrus linkages to reduce the radial dimensions required for a single Sarrus linkage to connect the malleus and the stapes.

Example 12

Figure 16:
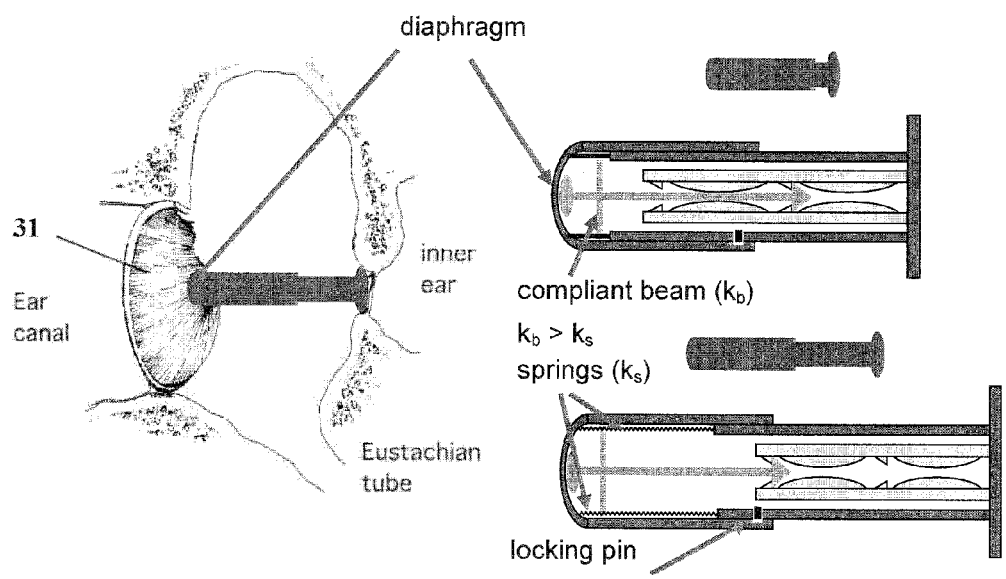
FIG. 16 shows a drawing of a compliant mechanism approach for an adjustable prosthesis in accordance with an embodiment.

Another embodiment uses a compliant mechanism internal to the outer cylindrical telescoping casing of the prosthesis, illustrated in FIG. 16. This mechanism decreases the prosthetic's external length incrementally by a ratcheting type actuation. That is, the prosthesis length can be ratcheted via a physician applying pressure to the eardrum which in turn induces motion similar to the operation of a click-pen. The compliance (denoted by stiffness $k_b$ and $k_s$) within the mechanism's structure provides spring forces, that upon removal of the physicians applied force on the prosthesis via pressure on the eardrum, pulls the end of the inner rod up against mechanical stops, a feature of the contoured beams inner profile. This inner rod is supported by the compliant beams with stiffness ($k_b$). The outer cylinder's diameter is of the order of 1 mm or less.

The prosthesis can be returned to its maximum length with the aid of internal springs $k_s$ and a release mechanism. The release mechanism can incorporate electromagnetic or mechanical means that spread radial outward the inner contoured beams slightly to allow the central rod supported by the compliant beams to pass without hooking (latching) on the mechanical stops of the contoured beams. For added protection, a locking pin can be integrated into the prosthesis to prevent accidental ratcheting of the prosthesis length due to exposure to extreme external noise levels.

Example 13

In order to reduce complexity and eliminate the need for difficult assembly the actuation of the prosthesis shaft can be induced by the physician pulling or pushing on the eardrum. In this embodiment, the prosthesis can be a solid shaft inside of a slightly larger hollowed outer shaft or tube, illustrated in FIG. 17. The inner shaft can be free to translate concentrically with respect to the outer shaft, changing the overall length.

Figure 18:
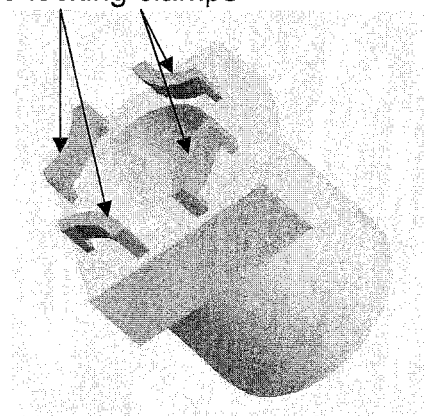
FIG. 18 shows a lock-collar mechanism for an adjustable prosthesis.
Figure 19:
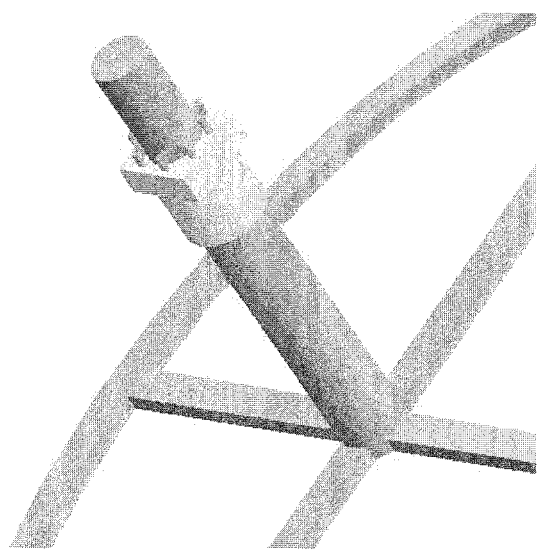
FIG. 19 shows an assembled adjustable middle ear prosthesis utilizing the lock-collar mechanism of FIG. 18.

The active element of the prosthesis can be a locking mechanism to prevent translation after the necessary adjustments have been made, for example as shown in FIGS. 18 and 19. The locking mechanism can include a collar made from bio compatible plastic that is affixed to the outer shaft. The collar can hold flexible tabs, that when closed can apply enough force to prevent motion of the inner shaft. When activated, the tabs can buckle away from the inner shaft allowing it to translate freely. A piezoelectric material can be used to provide a means of actuation.

Figure 20:
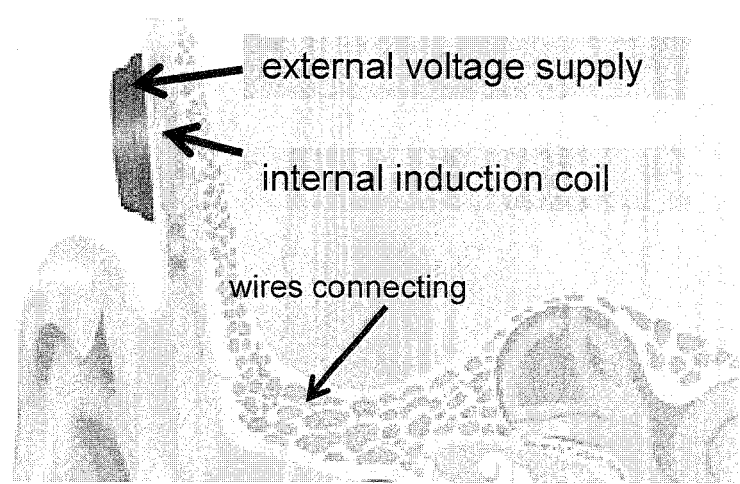
FIG. 20 shows a drawing for illustrating a technique of supplying voltage to a prosthesis.

The tabs can be constructed entirely from a bio compatible piezoelectric material or made from plastic with the piezoelectric material strategically embedded within. As illustrated in FIG. 20, an induction coil can be placed under the skin behind the patient's ear. This coil can have wires that lead to the piezoelectric elements in the prosthesis. The physician can place another coil over the embedded one behind the ear to supply the actuation voltage.

Another version may employ a collar that is constructed completely from a piezoelectric material and affixed to the outer shaft. Application of a voltage can cause the collar to dilate freeing the inner shaft and allowing translation. While powered off, the collar can constrict the inner shaft preventing any motion.

Experiment 1

An experiment was conducted to determine the relationship between clamping force and sliding force of the inner cylinder relative to the outer cylinder for an embodiment of the invention. This information provides an estimate of the forces required for realizing the functionality of the middle ear prosthesis. This data also provides values needed for sizing the inner diameter of the grips at the point of contact during clamping.

Equipment:

EFD Sample Syringes: Tip 32 gage (GA), yellow (acting as the inner cylinder with ID: 0.10 mm, OD: 0.23 mm), EFD Sample Syringes: Tip 25 GA, red (acting as the outer cylinder with ID: 0.25 mm, OD: 0.51 mm), AccuForce Cadet Force Gage (force readings in pounds, accurate to 0.01 pounds), Pair of 5 inch pliers, Newport work table (Syringe needles are calibrated by gauge, GA which refers to the diameter of the needle. Higher the GA number smaller is the diameter of the needle).

Experimental Setup:

The outer cylinder is held stationary by a clamp 15 that is bolted into the work table. The inner cylinder is attached to a thin wire that hung over a metal bar to form a pulley. Attached to the other end of the wire is the bottom half of a Styrofoam cup. The inner cylinder is then manually inserted into the outer cylinder.

Next, the tips of two 25 GA sample syringes are hot glued to the tips of pliers cross-wise as to create a single point of contact when the pliers are closed. The purpose of this is to recreate the Ti—Ti friction that will be found in the actual prosthesis. The pliers are then fixed in place such that when closed, the glued syringe tips clamp the inner cylinder.

Procedure:

The first objective was to find the force required on the inner cylinder to cause sliding. To do this, the pliers were left opened while water was added to the cup until the weight of the water overcame the friction forces of the cylinders and the inner cylinder slid out of the outer cylinder.

(It is noted that for this experiment and each of the following experiments that every time water was added to the cup the cup was supported such that the impact of the water being added did not cause the sliding. When the cup was supported, a small amount of water was added and then the cup was slowly released until its full weight was held by the friction in the cylinders. This process was repeated until sliding occurred.) Once the cup had been filled with enough water to induce sliding the weight of the cup and water was measured with the force gauge.

To check for accuracy, the force gauge was zeroed out and the weight of the cup and water were measured five times. Furthermore, this process was repeated with four combinations of inner and outer cylinders by using two different outer cylinders and two different inner cylinders to check the consistency of the results.

Next, the force gauge was used to apply a force on the grips of the pliers. The force gauge pushed down on the grips until the tips of the pliers had minimal contact with the inner cylinder (estimated as zero contact load condition, determined via visual inspection). The force gauge was then zeroed out to cancel out the resulting closing force required to overcome the spring in the pliers.

From knowledge of the dimensions of the pliers and the force reading from the force gauge, the clamping force on the inner cylinder was calculated. Similar to the previous procedure, water was added to the cup until sliding occurred. The weight of the cup and water was then measured. Also, as in the previous procedure, the weight of the cup and water was measured five times and the process was repeated with four combinations of inner and outer cylinders.

Lastly, the applied force applied via the force gauge was increased and the previous process was repeated twice yielding two different clamping forces.

With these data points, the force required for sliding was calculated as a function of the clamping force.

Results

Note: The force being exerted by the force transducer $F_1$ is not the actual force acting on the inner cylinder. To calculate the actual clamping force $F_2$ the distance between the point of application of force (by the transducer) and the pliers' center of rotation $r_1$ and the distance between the clamping end and the same center $r_2$ have to be calculated. The ratio of the forces would be equal to the ratio of these distances (by equating the moment).

$$F_1 r_1 = F_2 r_2$$

$$F_2 = (r_1/r_2) F_1$$

The ratio of $r_1$ to $r_2$ for the pliers was measured to be 4. Thus the actual clamping force will be 4 times the force applied using the force transducer.

Two red syringes (R1, R2) and two yellow syringes (Y1, Y2) were used to conduct the experiments and the average of the readings was calculated.

1. Unclamped Cylinders (Friction Between the Walls of the Cylinders)

Combinations of syringes were used and the average force required to start sliding between the two telescopic cylinders was determined. This force was applied at the end of the inner cylinder.

| Combination of syringes | Force required for sliding between cylinders | |
| --- | --- | --- |
| R1-Y1 | 0.04 lb | 0.04 lb |
|  | 0.04 lb | (0.18 N) |
|  | 0.04 lb |  |
|  | 0.04 lb |  |
|  | 0.04 lb |  |
| R1-Y2 | 0.025 lb | 0.025 lb |
|  | 0.025 lb | (0.11 N) |
|  | 0.025 lb |  |
|  | 0.025 lb |  |
|  | 0.025 lb |  |
| R2-Y1 | 0.045 lb | 0.045 lb |
|  | 0.045 lb | (0.20 N) |
|  | 0 045 lb |  |
|  | 0.045 lb |  |
|  | 0.045 lb |  |
| R2-Y2 | 0.025 lb | 0.025 lb |
|  | 0.025 lb | (0.11 N) |
|  | 0.025 lb |  |
|  | 0.025 lb |  |
|  | 0.025 lb |  |

Average force for sliding = 0.15 N

2. Telescopic Cylinders with Clamping Loads Applied to the Inner Cylinder

Case a) A known force of 0.11 lb is applied

| Combination of syringes | Measured force exerted by the transducer $F_1$ | Calculated clamping force on the inner cylinder $F_2$ | Measured force required for sliding between cylinders | |
| --- | --- | --- | --- | --- |
| R2-Y1 | 0.11 lb (0.49 N) | 0.11 lb (1.96 N) | 0.13 lb | 0.13 lb |
|  |  |  | 0.13 lb | (0.58 N) |
|  |  |  | 0.13 lb |  |
|  |  |  | 0.13 lb |  |
|  |  |  | 0.13 lb |  |

-continued

| Combination of syringes | Measured force exerted by the transducer $F_1$ | Calculated clamping force on the inner cylinder $F_2$ | Measured force required for sliding between cylinders | |
|---|---|---|---|---|
| R2-Y2 | 0.11 lb (0.49 N) | 0.11 lb (1.96 N) | 0.13 lb<br>0.13 lb<br>0.13 lb<br>0.13 lb<br>0.13 lb | 0.13 lb<br>(0.58 N) |

Case b) A known force of 0.25 lb is applied

| Combination of syringes | Force exerted by the transducer | Actual clamping force on the inner cylinder | Force required for sliding between cylinders | |
|---|---|---|---|---|
| R2-Y1 | 0.25 lb (1.11 N) | 1.00 lb (4.44 N) | 0.17 lb<br>0.17 lb<br>0.17 lb<br>0.17 lb<br>0.17 lb | 0.17 lb<br>(0.76 N) |
| R2-Y2 | 0.25 lb (1.11 N) | 1.00 lb (4.44 N) | 0.15 lb<br>0.15 lb<br>0.15 lb<br>0.15 lb<br>0.15 lb | 0.15 lb<br>(0.67 N) |

Case c) A known force of 0.37 lb is applied

| Combination of syringes | Force exerted by the transducer | Actual clamping force on the inner cylinder | Force required for sliding between cylinders | |
|---|---|---|---|---|
| R2-Y1 | 0.37 lb (1.65 N) | 1.47 lb (6.55 N) | 0.185 lb<br>0.185 lb<br>0.185 lb<br>0.185 lb<br>0.185 lb | 0.185 lb<br>(0.82 N) |
| R2-Y2 | 0.37 lb (1.65 N) | 1.47 lb (6.55 N) | 0.185 lb<br>0.185 lb<br>0.185 lb<br>0.185 lb<br>0.185 lb | 0.185 lb<br>(0.82 N) |

Average coefficient of friction was calculated by plotting the normal forces $F_2$ (actual clamping force on the inner cylinder) v/s the sliding forces and obtaining the slope of the linear fit for the plot.

Figure 21:
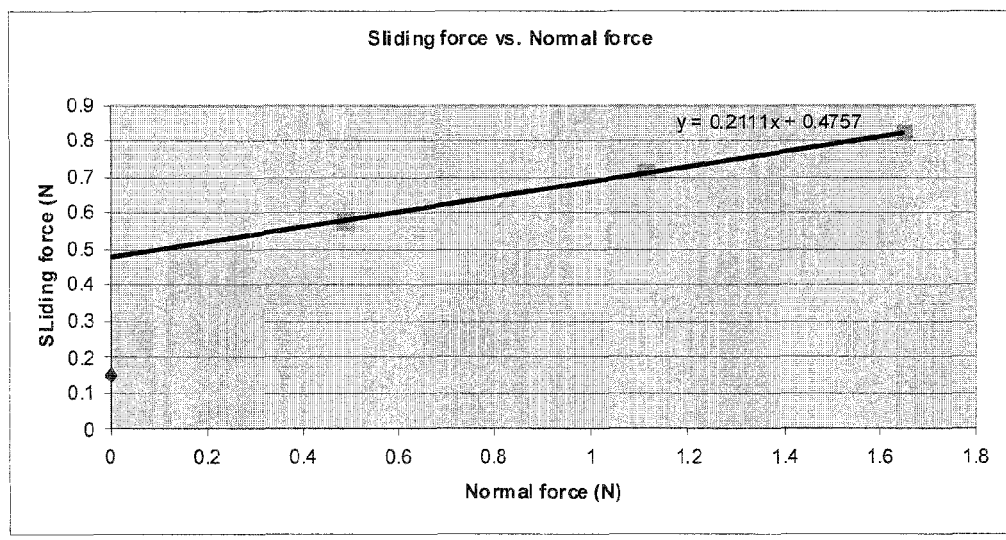
FIG. 21 shows a graph of sliding force vs. normal force.
Figure 22:
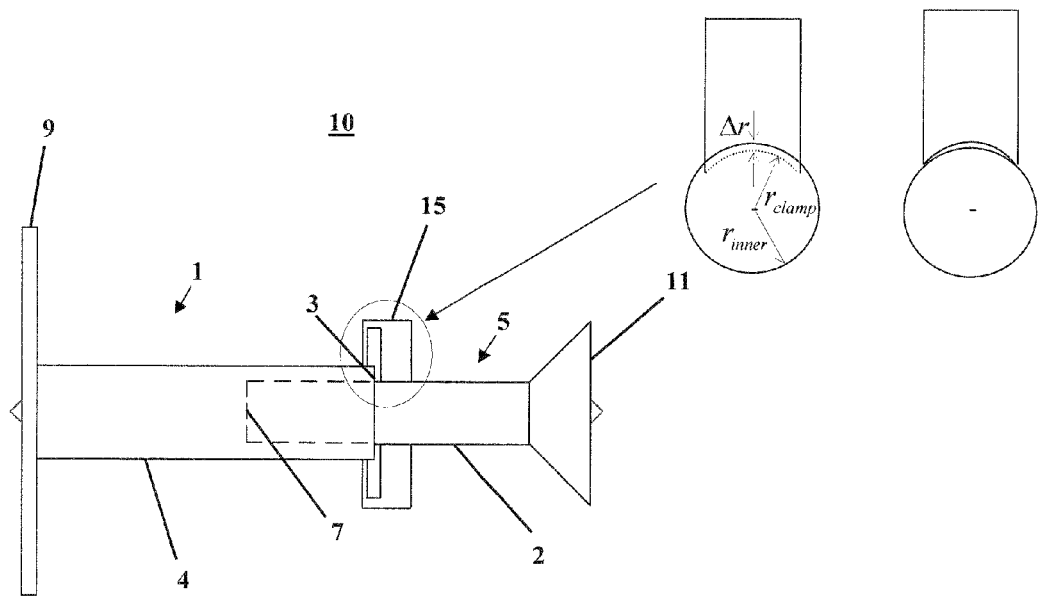
FIG. 22 shows the difference in radius of the clamp and outer radius of the inner cylinder.
Figure 23:
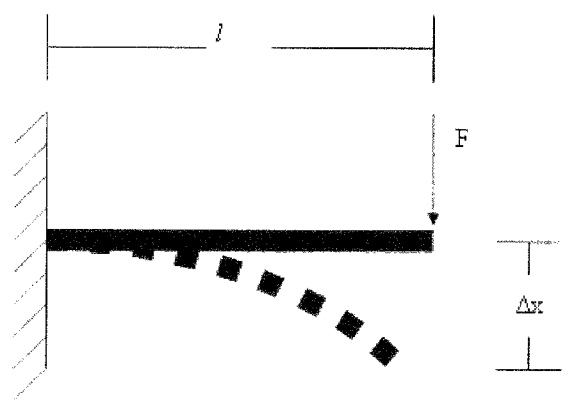
FIG. 23 shows beam deflection for a cantilever beam of length/with a fixed end and a force applied at the other end.
Figure 24:
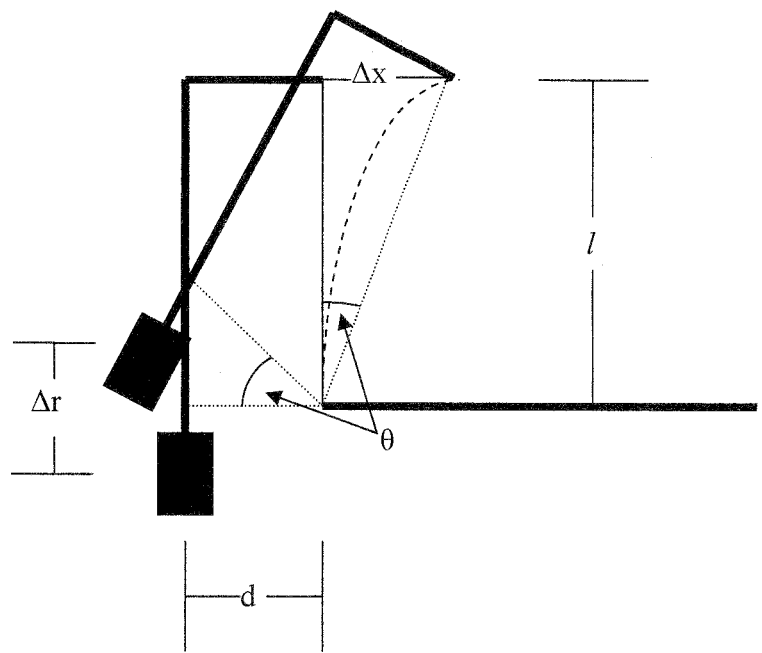
FIG. 24 shows the geometry of a clamp using the assumption of small angular deflection.
Figure 25:
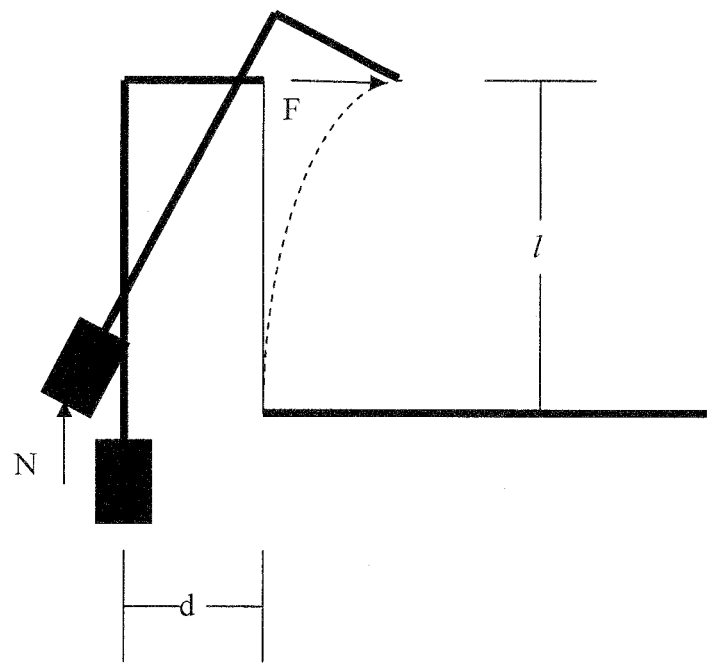
FIG. 25 shows an experimental static analysis.

Thus, from the graph shown in FIG. 21, the coefficient of friction is calculated as 0.21. Theoretically, the y-intercept should represent the constant friction force between the inner and outer cylinders. However, it is seen that the expected value of sliding force for no clamping greatly exceeds the experimental results. This could be due to the fact that when there is no clamping the two cylinders are only slightly touching and frictional forces are minimal. However, once clamping is applied, if the clamp 15 is not perfectly aligned then it could cause the inner cylinder to push up against the outer cylinder and create much greater frictional forces. In spite of these discrepancies in values, the results demonstrate the variability that can occur within the operation of the prosthesis. Furthermore, the results provide a nominal range of expected clamping force values for an embodiment of invention.

The inner cylinder and the clamp 15 are machined in such a way that there is a difference in the radius of the outer surface of the inner cylinder $r_{inner}$ and the radius of the inner surface of the clamp $r_{clamp}$. This dimensional difference in the radii called Δr results in the bending of the compliant beam 17 creating a clamping load that prevents the inner cylinder from moving relative to the outer cylinder; therefore, fixing the length of the prosthesis.

$$\Delta r = r_{inner} - r_{clamp}$$

This dimensional difference results in a horizontal force F being applied on the compliant beam 17 and a normal force N between the contact of the clamp 15 and the inner cylinder. The frictional force that is developed due to this normal force acts as the clamping force on the inner cylinder.

The relationship between these parameters can be easily determined using the following approach.

From beam deflection theory for a cantilever beam of length/with a fixed end and a force applied at the other end, the force required to deflect the free end by Δx is:

$$F = \frac{3EI\Delta x}{l^3}$$

Also, from the geometry of the clamp 15 and the assumption of small angular deflection, it is seen that:

$$\tan(\theta) \approx \frac{\Delta r}{d} \approx \frac{\Delta x}{l}$$

$$\therefore \Delta x \approx \frac{l\Delta r}{d}$$

Furthermore, from static analysis:

$$|Nd| = |Fl|$$

$$\therefore N = \frac{|F|l}{d}$$

Substituting yields:

$$N = \frac{Fl}{d}$$

$$= \frac{\left(\frac{3EI\Delta x}{l^3}\right)l}{d}$$

$$= \frac{3EI\Delta x}{dl^2}$$

$$= \frac{3EI\left(\frac{l\Delta r}{d}\right)}{dl^2}$$

$$= \frac{3EI\Delta r}{d^2 l}$$

From the models for the prosthesis, the values for the known parameters are:
d=0.06 mm
l=0.2 mm
E=110 GPa
I=2.5e−7

Using these constants, the following relationship is obtained between N and Δr:

$$N = 114.58 \Delta r$$

where N is in Newtons and Δr is in mm.

For a value of Δr=0.0005 mm, the normal force obtained is 0.0573 N

From the experimental results, the relationship between normal force and sliding force can be expressed as:

$$F_s = 0.21N + 0.48$$

Hence, for the calculated value of N the value of sliding force is 0.49 N. It is known from prior analysis that the applied force required of the electromagnet to bend the compliant beam 17 and thus unclamp the inner cylinder is in the order of 0.005 N. This 0.005 N value is much less than the above experimentally estimated minimal threshold value of 0.49 N required for sliding to occur. Thus, the experiments show that as the electromagnet creates a force on the tips of the clamping grips of the prosthesis, the clamping grips will bend and release the inner cylinder before sliding occurs.

Specific embodiments are described below.

Embodiment 1: A method of adjusting a middle ear prosthesis in situ, comprising:

positioning a middle ear prosthesis in a person's middle ear, wherein the middle ear prosthesis comprises:

a first element, wherein the first element has a first interconnecting end and a first contact end, wherein the first contact end is adapted to contact a first location of a person's middle ear; and a second element, wherein the second element has a second interconnecting end and a second contact end, wherein the second contact end is adapted to contact a second location of the person's middle ear, wherein the second interconnecting end is movably connected with the first interconnecting end such that a distance between the first contact end and the second contact end can be adjusted by moving the first interconnecting end with respect to the second interconnecting end; and a clamp, wherein the clamp is capable of releasably securing the first interconnected end to the second interconnected end, wherein the clamp comprises at least one clamp piece positioned on the first interconnecting end, wherein each clamp piece comprises a compliant part and a clamp head, wherein the compliant part holds the clamp head against the second interconnecting end when the second interconnecting end is inserted into the first interconnecting end and the compliant part is in an equilibrium position, wherein each clamp piece comprises an actuation portion, wherein upon exposure of the actuation portion to a magnetic field having a component in a certain direction of at least a threshold value, a force is applied to the compliant portion so as to pull the head clamp away from contact with the second interconnecting end so as to allow the first interconnecting end and second interconnecting end to move with respect to each other; and actuating the clamp so as to allow the first interconnecting end to move with respect to the second interconnecting end;

adjusting the distance between the first contact end and the second contact end by moving the first interconnecting end with respect to the second interconnecting end.

Embodiment 2: Embodiment 1, wherein actuating the clamp comprises exposing the actuation portion to a magnetic field having a component in the certain direction of at least the threshold value.

Embodiment 3: Embodiment 1, wherein the first interconnecting end and the second interconnecting end are slidably connected such that when the first interconnecting end slides with respect to the second interconnecting end, the distance between the first contact end and the second contact end is adjusted.

Embodiment 4: Embodiment 1, wherein the first interconnecting end and the second interconnecting end are connected in a telescoping manner such that when the first interconnecting end slides with respect to the second interconnecting end, the distance between the first contact end and the second contact end is adjusted.

Embodiment 5: Embodiment 1, wherein the first interconnecting end and the second interconnecting end are rotatably connected such that when the first interconnecting end rotates with respect to the second interconnecting end, the distance between the first contact end and the second contact end is adjusted.

Embodiment 6: Embodiment 1, wherein the first interconnecting end and the second interconnecting end are threadably connected such that when the first interconnecting end is rotated with respect to the second interconnecting end, the distance between the first contact end and the second contact end is adjusted.

Embodiment 7: Embodiment 1, wherein the first interconnecting end comprises a bore into which the second interconnecting end is inserted.

Embodiment 8: Embodiment 1, wherein the force tends to move the prosthesis toward the first contact end.

Embodiment 9: Embodiment 1, wherein the clamp comprises a plurality of clamp pieces positioned symmetrically around the first interconnecting end of the first element.

Embodiment 10: Embodiment 1, wherein the clamp comprises two clamp pieces on opposite sides of the first interconnected end.

Embodiment 11: Embodiment 1, further comprising a hermetically-sealed casing, wherein the hermetically-sealed casing surrounds the clamp and makes a hermetic seal with the first interconnecting end and makes a hermetic seal with the second interconnecting end.

Embodiment 12: Embodiment 1, wherein the clamp is integral with the first interconnecting end.

Embodiment 13: Embodiment 1, wherein the clamp comprises at least one clamp head, wherein at least a portion of one or more of the at least one clamp head has a radius with respect to a longitudinal axis of the first interconnecting end smaller than a radius of an inner surface of the first interconnecting end with respect to the longitudinal axis of the first interconnecting end.

Embodiment 14: Embodiment 1, wherein a gap between an inner surface of the first interconnecting end and an outer surface of the second interconnecting end is less than 0.002 mm.

Embodiment 15: Embodiment 1, wherein the actuation portion comprises a magnetic material.

Embodiment 16: Embodiment 1, wherein the actuation portion comprises a magnet.

Embodiment 17: Embodiment 1, wherein the prosthesis further comprises a counter force portion, wherein upon exposure of the counter force portion to the magnetic field having the component in the certain direction a second force is applied to the prosthesis, wherein the second force has a component in an opposite direction to the force applied to the compliant portion.

Embodiment 18: Embodiment 17, wherein the component of the second force has a magnitude within 5% of a magnitude of the force applied to the compliant portion.

Embodiment 19: Embodiment 17, wherein the second force is applied to the compliant part.

Embodiment 20: Embodiment 1, wherein the prosthesis has an unextended position where the distance between the first contact end and the second contact end is a minimum distance and an extended position where the distance between the first contact end and the second contact end is a maximum distance.

Embodiment 21: Embodiment 1, wherein the minimum distance is in a range from 1 mm to 8 mm and the maximum distance is in a range from 1.5 mm to 15 mm.

Embodiment 22: Embodiment 1, wherein the prosthesis comprises titanium.

Embodiment 23: Embodiment 1, wherein the prosthesis is made of titanium and at least one volume of a material that when exposed to a magnetic field experiences a force on the volume of the material.

Embodiment 24: Embodiment 1, wherein the second element has a length in the range from 0.5 mm to 8 mm.

Embodiment 25: Embodiment 1, wherein the first element has a length in the range from 0.5 mm to 8 mm.

Embodiment 26: Embodiment 1, wherein the second contact end is approximately conically shaped, wherein the first contact end has an approximately elliptically shaped transverse cross-section.

Embodiment 27: Embodiment 1, wherein the first interconnected end has a cylindrical transverse cross-sectional shape, wherein the second interconnected end has a cylindrical cross-sectional shape.

Embodiment 28: Embodiment 26, wherein the first contact end has a length less than 3 mm.

Embodiment 29: Embodiment 26, wherein the first contact end has a maximum diameter in the range of 0.1 mm to 8 mm.

Embodiment 30: Embodiment 26, wherein the second contact end has a length less than 3 mm.

Embodiment 31: Embodiment 26, wherein a distal end of the second contact end has a diameter in the range of 0.1 mm to 8 mm.

Embodiment 32: Embodiment 26, where the first contact end has one more apertures therethrough from a proximal end to a distal end of the first contact end.

Embodiment 33: Embodiment 1, wherein an antimicrobial texture is applied to an outer surface to prevent microbial growth.

Embodiment 34: Embodiment 1, wherein an antimicrobial coating is applied to an outer surface to prevent microbial growth.

Embodiment 35: Embodiment 33, wherein an antimicrobial texture is applied to an inner surface to prevent microbial growth.

Embodiment 36: Embodiment 34, wherein an antimicrobial coating is applied to an inner surface to prevent microbial growth.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

The invention claimed is:

1. A middle ear prosthesis, comprising:
   a first element, wherein the first element has a first interconnecting end and a first contact end, wherein the first contact end is adapted to contact a first location of a person's middle ear;
   a second element, wherein the second element has a second interconnecting end and a second contact end, wherein the second contact end is adapted to contact a second location of the person's middle ear, wherein the second interconnecting end is movably connected with the first interconnecting end such that a distance between the first contact end and the second contact end can be adjusted by moving the first interconnecting end with respect to the second interconnecting end; and
   a clamp, wherein the clamp is capable of releasably securing the first interconnected end to the second interconnected end, wherein the clamp comprises at least one clamp piece positioned on the first interconnecting end, wherein each clamp piece comprises a compliant portion and a clamp head, wherein the compliant portion holds the clamp head against the second interconnecting end when the second interconnecting end is inserted into the first interconnecting end and the compliant portion is in an equilibrium position, wherein each clamp piece comprises a magnetic material, wherein upon exposure of the clamp piece to a magnetic field having a component in a certain direction of at least a threshold value, a force is applied to the compliant portion so as to pull the clamp head away from contact with the second interconnecting end so as to allow the first interconnecting end and second interconnecting end to move with respect to each other.

2. The prosthesis according to claim 1, wherein the first interconnecting end and the second interconnecting end are connected in a telescoping manner such that when the first interconnecting end slides with respect to the second interconnecting end, the distance between the first contact end and the second contact end is adjusted.

3. The prosthesis according to claim 1, wherein the first interconnecting end and the second interconnecting end are rotatably connected such that when the first interconnecting end rotates with respect to the second interconnecting end, the distance between the first contact end and the second contact end is adjusted.

4. The prosthesis according to claim 3, wherein the first interconnecting end and the second interconnecting end are threadably connected such that when the first interconnecting end is rotated with respect to the second interconnecting end, the distance between the first contact end and the second contact end is adjusted.

5. The prosthesis according to claim 1, wherein the first interconnecting end comprises a bore into which the second interconnecting end is inserted.

6. The prosthesis according to claim 1, wherein the force tends to move the prosthesis toward the first contact end.

7. The prosthesis according to claim 1, wherein the clamp comprises a plurality of clamp pieces positioned symmetrically around the first interconnecting end of the first element.

8. The prosthesis according to claim 1, wherein the clamp comprises two clamp pieces on opposite sides of the first interconnected end.

9. A middle ear prosthesis, comprising:
   a first element, wherein the first element has a first interconnecting end and a first contact end, wherein the first contact end is adapted to contact a first location of a person's middle ear;
   a second element, wherein the second element has a second interconnecting end and a second contact end, wherein the second contact end is adapted to contact a second location of the person's middle ear, wherein the second interconnecting end is movably connected with the first interconnecting end such that a distance between the first contact end and the second contact end can be adjusted by moving the first interconnecting end with respect to the second interconnecting end;

a clamp, wherein the clamp is capable of releasably securing the first interconnected end to the second interconnected end, wherein the clamp comprises at least one clamp piece positioned on the first interconnecting end, wherein each clamp piece comprises a compliant portion and a clamp head, wherein the compliant portion holds the clamp head against the second interconnecting end when the second interconnecting end is inserted into the first interconnecting end and the compliant portion is in an equilibrium position, wherein each clamp piece comprises a magnetic material or magnet, wherein upon exposure of the clamp piece to a magnetic field having a component in a certain direction of at least a threshold value, a force is applied to the compliant portion so as to pull the clamp head away from contact with the second interconnecting end so as to allow the first interconnecting end and second interconnecting end to move with respect to each other; and a hermetically-sealed casing, wherein the hermetically-sealed casing surrounds the clamp and makes a hermetic seal with the first interconnecting end and makes a hermetic seal with the second interconnecting end.

10. The prosthesis according to claim 1, wherein the clamp is integral with the first interconnecting end.

11. The prosthesis according to claim 1, wherein the clamp comprises at least one clamp head, wherein at least a portion of one or more of the at least one clamp head has a radius with respect to a longitudinal axis of the first interconnecting end smaller than a radius of an inner surface of the first interconnecting end with respect to the longitudinal axis of the first interconnecting end.

12. The prosthesis according to claim 11, wherein a gap between an inner surface of the first interconnecting end and an outer surface of the second interconnecting end is less than 0.002 mm.

13. The prosthesis according to claim 1, wherein the first interconnecting end and the second interconnecting end are slidably connected such that when the first interconnecting end slides with respect to the second interconnecting end, the distance between the first contact end and the second contact end is adjusted.

14. A middle ear prosthesis, comprising:

a first element, wherein the first element has a first interconnecting end and a first contact end, wherein the first contact end is adapted to contact a first location of a person's middle ear;

a second element, wherein the second element has a second interconnecting end and a second contact end, wherein the second contact end is adapted to contact a second location of the person's middle ear, wherein the second interconnecting end is movably connected with the first interconnecting end such that a distance between the first contact end and the second contact end can be adjusted by moving the first interconnecting end with respect to the second interconnecting end; and a clamp, wherein the clamp is capable of releasably securing the first interconnected end to the second interconnected end, wherein the clamp comprises at least one clamp piece positioned on the first interconnecting end, wherein each clamp piece comprises a compliant portion and a clamp head, wherein the compliant portion holds the clamp head against the second interconnecting end when the second interconnecting end is inserted into the first interconnecting end and the compliant portion is in an equilibrium position, wherein each clamp piece comprises a magnet, wherein upon exposure of the clamp piece to a magnetic field having a component in a certain direction of at least a threshold value, a force is applied to the compliant portion so as to pull the clamp head away from contact with the second interconnecting end so as to allow the first interconnecting end and second interconnecting end to move with respect to each other.

15. The prosthesis according to claim 1, further comprising a counter force portion, wherein upon exposure of the counter force portion to the magnetic field having the component in the certain direction a second force is applied to the prosthesis, wherein the second force has a component in an opposite direction to the force applied to the compliant portion.

16. The prosthesis according to claim 15, wherein the component of the second force has a magnitude within 5% of a magnitude of the force applied to the compliant portion.

17. The prosthesis according to claim 15, wherein the second force is applied to the compliant portion.

18. The prosthesis according to claim 1, wherein the prosthesis has an unextended position where the distance between the first contact end and the second contact end is a minimum distance and an extended position where the distance between the first contact end and the second contact end is a maximum distance.

19. The prosthesis according to claim 1, wherein the minimum distance is in a range from 1 mm to 8 mm and the maximum distance is in a range from 1.5 mm to 15 mm.

20. The prosthesis according to claim 1, wherein the prosthesis comprises titanium.

21. The prosthesis according to claim 1, wherein the prosthesis is made of titanium and at least one volume of a material that when exposed to a magnetic field experiences a force on the volume of the material.

22. The prosthesis according to claim 1, wherein the second element has a length in the range from 0.5 mm to 8 mm.

23. The prosthesis according to claim 1, wherein the first element has a length in the range from 0.5 mm to 8 mm.

24. The prosthesis according to claim 1, wherein the second contact end is approximately conically shaped, wherein the first contact end has an approximately elliptically shaped transverse cross-section.

25. The prosthesis according to claim 1, wherein the first interconnected end has a cylindrical transverse cross-sectional shape, wherein the second interconnected end has a cylindrical cross-sectional shape.

26. The prosthesis according to claim 24, wherein the first contact end has a length less than 3 mm.

27. The prosthesis according to claim 24, wherein the first contact end has a maximum diameter in the range of 0.1 mm to 8 mm.

28. The prosthesis according to claim 24, wherein the second contact end has a length less than 3 mm.

29. The prosthesis according to claim 24, wherein a distal end of the second contact end has a diameter in the range of 0.1 mm to 8 mm.

30. The prosthesis according to claim 24, where the first contact end has one or more apertures therethrough from a proximal end to a distal end of the first contact end.

31. The prosthesis according to claim 1, wherein an antimicrobial texture is applied to an outer surface to prevent microbial growth.

32. The prosthesis according to claim 1, wherein an antimicrobial coating is applied to an outer surface to prevent microbial growth.

33. The prosthesis according to claim 31, wherein an antimicrobial texture is applied to an inner surface to prevent microbial growth.

34. The prosthesis according to claim 32, wherein an antimicrobial coating is applied to an inner surface to prevent microbial growth.

35. A method of adjusting a middle ear prosthesis in situ, comprising:
positioning a middle ear prosthesis in a person's middle ear, wherein the middle ear prosthesis comprises:
a first element, wherein the first element has a first interconnecting end and a first contact end, wherein the first contact end is adapted to contact a first location of a person's middle ear; and
a second element, wherein the second element has a second interconnecting end and a second contact end, wherein the second contact end is adapted to contact a second location of the person's middle ear, wherein the second interconnecting end is movably connected with the first interconnecting end such that a distance between the first contact end and the second contact end can be adjusted by moving the first interconnecting end with respect to the second interconnecting end; and
a clamp, wherein the clamp is capable of releasably securing the first interconnected end to the second interconnected end, wherein the clamp comprises at least one clamp piece positioned on the first interconnecting end, wherein each clamp piece comprises a compliant portion and a clamp head, wherein the compliant portion holds the clamp head against the second interconnecting end when the second interconnecting end is inserted into the first interconnecting end and the compliant portion is in an equilibrium position, wherein each clamp piece comprises a magnetic material, wherein upon exposure of the clamp piece to a magnetic field having a component in a certain direction of at least a threshold value, a force is applied to the compliant portion so as to pull the clamp head away from contact with the second interconnecting end so as to allow the first interconnecting end and second interconnecting end to move with respect to each other; and
actuating the clamp so as to allow the first interconnecting end to move with respect to the second interconnecting end;
adjusting the distance between the first contact end and the second contact end by moving the first interconnecting end with respect to the second interconnecting end.

36. The method according to claim 35, wherein actuating the clamp comprises exposing the clamp piece to a magnetic field having a component in the certain direction of at least the threshold value.

37. The method according to claim 35, wherein the first interconnecting end and the second interconnecting end are slidably connected such that when the first interconnecting end slides with respect to the second interconnecting end, the distance between the first contact end and the second contact end is adjusted.

38. The method according to claim 35, wherein the first interconnecting end and the second interconnecting end are connected in a telescoping manner such that when the first interconnecting end slides with respect to the second interconnecting end, the distance between the first contact end and the second contact end is adjusted.

39. The method according to claim 35, wherein the first interconnecting end and the second interconnecting end are rotatably connected such that when the first interconnecting end rotates with respect to the second interconnecting end, the distance between the first contact end and the second contact end is adjusted.

40. The method according to claim 39, wherein the first interconnecting end and the second interconnecting end are threadably connected such that when the first interconnecting end is rotated with respect to the second interconnecting end, the distance between the first contact end and the second contact end is adjusted.

41. The method according to claim 35, wherein the first interconnecting end comprises a bore into which the second interconnecting end is inserted.

42. The method according to claim 35, wherein the force tends to move the prosthesis toward the first contact end.

43. The method according to claim 35, wherein the clamp comprises a plurality of clamp pieces positioned symmetrically around the first interconnecting end of the first element.

44. The method according to claim 35, wherein the clamp comprises two clamp pieces on opposite sides of the first interconnected end.

45. The method according to claim 35, further comprising a hermetically-sealed casing, wherein the hermetically-sealed casing surrounds the clamp and makes a hermetic seal with the first interconnecting end and makes a hermetic seal with the second interconnecting end.

46. The method according to claim 35, wherein the clamp is integral with the first interconnecting end.

47. The method according to claim 35, wherein the clamp comprises at least one clamp head, wherein at least a portion of one or more of the at least one clamp head has a radius with respect to a longitudinal axis of the first interconnecting end smaller than a radius of an inner surface of the first interconnecting end with respect to the longitudinal axis of the first interconnecting end.

48. The method according to claim 47, wherein a gap between an inner surface of the first interconnecting end and an outer surface of the second interconnecting end is less than 0.002 mm.

49. The method according to claim 35, wherein each clamp piece comprises a magnet.

50. The method according to claim 35, wherein the prosthesis further comprises a counter force portion, wherein upon exposure of the counter force portion to the magnetic field having the component in the certain direction a second force is applied to the prosthesis, wherein the second force has a component in an opposite direction to the force applied to the compliant portion.

51. The method according to claim 50, wherein the component of the second force has a magnitude within 5% of a magnitude of the force applied to the compliant portion.

52. The method according to claim 50, wherein the second force is applied to the compliant portion.

53. The method according to claim 35, wherein the prosthesis has an unextended position where the distance between the first contact end and the second contact end is a minimum distance and an extended position where the distance between the first contact end and the second contact end is a maximum distance.

54. The method according to claim 35, wherein the minimum distance is in a range from 1 mm to 8 mm and the maximum distance is in a range from 1.5 mm to 15 mm.

55. The method according to claim 35, wherein the prosthesis comprises titanium.

56. The method according to claim 35, wherein the prosthesis is made of titanium and at least one volume of a material that when exposed to a magnetic field experiences a force on the volume of the material.

57. The method according to claim 35, wherein the second element has a length in the range from 0.5 mm to 8 mm.

58. The method according to claim 35, wherein the first element has a length in the range from 0.5 mm to 8 mm.

59. The method according to claim 35, wherein the second contact end is approximately conically shaped, wherein the first contact end has an approximately elliptically shaped transverse cross-section.

60. The method according to claim 35, wherein the first interconnected end has a cylindrical transverse cross-sectional shape, wherein the second interconnected end has a cylindrical cross-sectional shape.

61. The method according to claim 59, wherein the first contact end has a length less than 3 mm.

62. The method according to claim 59, wherein the first contact end has a maximum diameter in the range of 0.1 mm to 8 mm.

63. The method according to claim 59, wherein the second contact end has a length less than 3 mm.

64. The method according to claim 59, wherein a distal end of the second contact end has a diameter in the range of 0.1 mm to 8 mm.

65. The method according to claim 59, where the first contact end has one or more apertures therethrough from a proximal end to a distal end of the first contact end.

66. The method according to claim 35, wherein an antimicrobial texture is applied to an outer surface to prevent microbial growth.

67. The method according to claim 35, wherein an antimicrobial coating is applied to an outer surface to prevent microbial growth.

68. The method according to claim 66, wherein an antimicrobial texture is applied to an inner surface to prevent microbial growth.

69. The method according to claim 67, wherein an antimicrobial coating is applied to an inner surface to prevent microbial growth.

70. A method of adjusting a middle ear prosthesis in situ, comprising:
   positioning a middle ear prosthesis in a person's middle ear, wherein the middle ear prosthesis comprises:
      a first element, wherein the first element has a first interconnecting end and a first contact end, wherein the first contact end is adapted to contact a first location of a person's middle ear; and
      a second element, wherein the second element has a second interconnecting end and a second contact end, wherein the second contact end is adapted to contact a second location of the person's middle ear, wherein the second interconnecting end is movably connected with the first interconnecting end such that a distance between the first contact end and the second contact end can be adjusted by moving the first interconnecting end with respect to the second interconnecting end; and
      a clamp, wherein the clamp is capable of releasably securing the first interconnected end to the second interconnected end, wherein the clamp comprises at least one clamp piece positioned on the first interconnecting end, wherein each clamp piece comprises a compliant portion and a clamp head, wherein the compliant portion holds the clamp head against the second interconnecting end when the second interconnecting end is inserted into the first interconnecting end and the compliant portion is in an equilibrium position, wherein each clamp piece comprises a magnet, wherein upon exposure of the clamp piece to a magnetic field having a component in a certain direction of at least a threshold value, a force is applied to the compliant portion so as to pull the clamp head away from contact with the second interconnecting end so as to allow the first interconnecting end and second interconnecting end to move with respect to each other; and
   actuating the clamp so as to allow the first interconnecting end to move with respect to the second interconnecting end;
   adjusting the distance between the first contact end and the second contact end by moving the first interconnecting end with respect to the second interconnecting end.

71. A method of adjusting a middle ear prosthesis in situ, comprising:
   positioning a middle ear prosthesis in a person's middle ear, wherein the middle ear prosthesis comprises:
      a first element, wherein the first element has a first interconnecting end and a first contact end, wherein the first contact end is adapted to contact a first location of a person's middle ear; and
      a second element, wherein the second element has a second interconnecting end and a second contact end, wherein the second contact end is adapted to contact a second location of the person's middle ear, wherein the second interconnecting end is movably connected with the first interconnecting end such that a distance between the first contact end and the second contact end can be adjusted by moving the first interconnecting end with respect to the second interconnecting end; and
      a clamp, wherein the clamp is capable of releasably securing the first interconnected end to the second interconnected end, wherein the clamp comprises at least one clamp piece positioned on the first interconnecting end, wherein each clamp piece comprises a compliant portion and a clamp head, wherein the compliant portion holds the clamp head against the second interconnecting end when the second interconnecting end is inserted into the first interconnecting end and the compliant portion is in an equilibrium position, wherein each clamp piece comprises a magnetic material or a magnet, wherein upon exposure of the clamp piece to a magnetic field having a component in a certain direction of at least a threshold value, a force is applied to the compliant portion so as to pull the clamp head away from contact with the second interconnecting end so as to allow the first interconnecting end and second interconnecting end to move with respect to each other; and
      a hermetically-sealed casing, wherein the hermetically-sealed casing surrounds the clamp and makes a hermetic seal with the first interconnecting end and makes a hermetic seal with the second interconnecting end;
   actuating the clamp so as to allow the first interconnecting end to move with respect to the second interconnecting end;
   adjusting the distance between the first contact end and the second contact end by moving the first interconnecting end with respect to the second interconnecting end.

* * * * *

UNITED STATES PATENT AND TRADEMARK OFFICE
CERTIFICATE OF CORRECTION

PATENT NO. : 8,435,291 B2
APPLICATION NO. : 12/936036
DATED : May 7, 2013
INVENTOR(S) : Gloria Jean Wiens et al.

It is certified that error appears in the above-identified patent and that said Letters Patent is hereby corrected as shown below:

In the Specifications

Column 1,
Line 12, "which is are hereby" should read --which are hereby--.
Line 45, "TTPT™-VARIAC" should read --TTP™-VARIAC--.

Column 4,
Lines 17-18, "embodiment the" should read --embodiment, the--.

Column 8,
Line 58, "less from" should read --less than from--.
Line 60, "less from" should read --less than from--.
Line 65, "less from" should read --less than from--.
Line 67, "cylinder from" should read --cylinder can be from--.

Column 11,
Line 22, "it is same as" should read --it is the same as--.
Line 34, "into to the outer" should read --into the outer--.

Column 12,
Lines 13-14, "in future," should read --in the future,--.

Column 13,
Line 12, "In a previous" should read --In previous--.

Signed and Sealed this
Twenty-fourth Day of December, 2013

Margaret A. Focarino
*Commissioner for Patents of the United States Patent and Trademark Office*